United States Patent
Ryan et al.

(10) Patent No.: US 7,741,014 B2
(45) Date of Patent: Jun. 22, 2010

(54) PATTERNING AND ALTERATION OF MOLECULES

(75) Inventors: Declan Ryan, Cahirdown (IE); Babak Amir-Parviz, Seattle, WA (US); Vincent Linder, Renens (CH); Vincent Semetey, Le Mans (FR); Samuel K. Sia, New York, NY (US); George M. Whitesides, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 595 days.

(21) Appl. No.: 11/401,485

(22) Filed: Apr. 10, 2006

(65) Prior Publication Data

US 2007/0000866 A1 Jan. 4, 2007

Related U.S. Application Data

(63) Continuation of application No. 11/222,500, filed on Sep. 8, 2005, now abandoned.

(60) Provisional application No. 60/622,187, filed on Oct. 26, 2004.

(51) Int. Cl.
*G03F 7/00* (2006.01)
*H01L 21/302* (2006.01)

(52) U.S. Cl. .............................. 430/311; 430/322; 430/5

(58) Field of Classification Search .................. 430/322, 430/5, 311
See application file for complete search history.

(56) References Cited

U.S. PATENT DOCUMENTS

| | | | |
|---|---|---|---|
| 5,512,131 A | 4/1996 | Kumar et al. | |
| 5,514,501 A * | 5/1996 | Tarlov | 430/5 |
| 5,620,850 A | 4/1997 | Bamdad et al. | |
| 5,776,748 A | 7/1998 | Singhvi et al. | |

(Continued)

FOREIGN PATENT DOCUMENTS

WO    WO 97/44692    11/1997

(Continued)

OTHER PUBLICATIONS

Brewer, N., et al., "Oxidation of Self-Assembled Monolayers by UV Light with a Wavelength of 254 nm", J. Am. Chem. Soc., 2001, 123, pp. 4089-4090.

(Continued)

*Primary Examiner*—Kathleen Duda
*Assistant Examiner*—Caleen O Sullivan
(74) *Attorney, Agent, or Firm*—Wolf, Greenfield & Sacks, P.C.

(57) ABSTRACT

A series of methods, compositions, and articles for patterning a surface with multiple, aligned layers of molecules, by exposing the molecules to electromagnetic radiation is provided. In certain embodiments, a single photomask acts as an area-selective filter for light at multiple wavelengths. A single set of exposures of multiple wavelengths through this photomask may make it possible to fabricate a pattern comprising discontinuous multiple regions, where the regions differ from each other in at least one chemical and/or physical property, without acts of alignment between the exposures. In certain embodiments, the surface includes molecules attached thereto that can be photocleaved upon exposure to a certain wavelength of radiation, thereby altering the chemical composition on at least a portion of the surface.

30 Claims, 9 Drawing Sheets

U.S. PATENT DOCUMENTS

| | | | |
|---|---|---|---|
| 5,976,826 | A | 11/1999 | Singhvi et al. |
| 6,180,239 | B1 | 1/2001 | Whitesides et al. |
| 6,197,515 | B1 | 3/2001 | Bamdad et al. |
| 6,355,198 | B1 | 3/2002 | Kim et al. |
| 6,368,838 | B1 | 4/2002 | Singhvi et al. |
| 6,518,168 | B1 | 2/2003 | Clem et al. |
| 6,645,432 | B1 | 11/2003 | Anderson et al. |
| 6,686,184 | B1 | 2/2004 | Anderson et al. |
| 6,776,094 | B1 | 8/2004 | Whitesides et al. |
| 6,893,850 | B2 | 5/2005 | Ostuni et al. |
| 7,282,240 | B1 | 10/2007 | Jackman et al. |
| 2002/0084252 | A1* | 7/2002 | Buchwalter et al. ........... 216/44 |
| 2002/0094572 | A1 | 7/2002 | Singhvi et al. |
| 2003/0030184 | A1* | 2/2003 | Kim et al. .................... 264/325 |
| 2003/0124509 | A1 | 7/2003 | Kenis et al. |
| 2003/0156992 | A1 | 8/2003 | Anderson et al. |
| 2004/0121066 | A1 | 6/2004 | Anderson et al. |
| 2004/0159633 | A1 | 8/2004 | Whitesides et al. |
| 2006/0063276 | A1 | 3/2006 | Jiang et al. |
| 2006/0138083 | A1 | 6/2006 | Ryan et al. |
| 2006/0257792 | A1* | 11/2006 | Krause et al. ................ 430/313 |

FOREIGN PATENT DOCUMENTS

| | | |
|---|---|---|
| WO | WO 2004/067191 A2 | 8/2004 |

OTHER PUBLICATIONS

Dillmore, W. S., et al., "A Photochemical Method for Patterning the Immobilization of Ligands and Cells to Self-Assembled Monolayers", Langmuir 2004, 20, 7223-7231.

Holden, M., et al., "Light Activated Patterning of Dye-Labeled Molecules on Surfaces", J. Am. Chem. Soc. 2003, 125, pp. 8074-8075.

Love, J.C., et al., "Self-Assembled Monolayers of Alkanethiolates on Palladium Are Good Etch Resists", J. Am. Chem. Soc., vol. 124, No. 8, 2002, pp. 1576-1577.

Marriott, G., et al., "Caged peptides and proteins: new probes to study polypeptide function in complex biological systems", Trends in Plant Science, Aug. 1999, vol. 4, No. 8, pp. 330-334.

Pease, A.C., et al., "Light-generated oligonucleotide arrays for rapid DNA sequence analysis", Proc. Natl. Acad. Sci. USA, May 1994, vol. 91, pp. 5022-5026.

Ryan, D., "Patterning Multiple Aligned Self-Assembled Monolayers Using Light", Langmuir 2004, 20, 9080-9088.

Singh-Gasson, S., et al., "Maskless fabrication of light-directed oligonucleotide microarrays using a digital micromirror array", Nature Biotechnology, vol. 17, Oct. 1999, pp. 974-978.

Tien, J., et al., "Fabrication of aligned microstructures with a single elastomeric stamp", PNAS, Feb. 2002, vol. 99, No. 4, pp. 1758-1762.

Uchida, K., et al., "Multifrequency Photochromic Recording and Nondestructive Readout using IR Light", CHEMPHYSCHEM 2003, 4, pp. 1124-1127.

* cited by examiner

..... 220 nm exposure (%ML = 118%)
- - HS(CH$_2$)$_{15}$CH$_3$ (%ML = 100%)
- · 365 nm exposure (%ML = 4.0%)
— No exposure (%ML = 1.2%)

PATTERNING AND ALTERATION OF MOLECULES

RELATED APPLICATIONS

This application is a continuation of U.S. patent application Ser. No. 11/222,500, entitled "Patterning and Alternation of Molecules", filed Sep. 8, 2005 now abandoned, which claims priority under 35 U.S.C. §119(e) to U.S. Provisional Application Ser. No. 60/622,187, entitled "Patterning and Alternation of Molecules", filed on Oct. 26, 2004.

FEDERALLY SPONSORED RESEARCH

Various aspects of the present invention were supported by a grant from the National Institutes of Health (No. GM065364). The Government has certain rights in the invention.

FIELD OF THE INVENTION

This invention generally relates to the alteration of the molecules of a surface, and more specifically, to the alteration of the molecules of a surface by photocleavage of the molecules.

BACKGROUND

The ability to produce complex patterns of molecules on surfaces is important for understanding a number of different phenomena including dewetting, adhesion, cell-surface interactions, and cell-cell interactions; it is also significant for developing applications in biology and biochemistry, such as assays, microarrays, and devices for high-throughput screening.

Several techniques allow the alignment of molecules, and in particular, the alignment of SAMs, on surfaces. Microcontact printing (μCP) of alkanethiols on a gold or silver surface using a poly(dimethylsiloxane) (PDMS) stamp allows one type of alkanethiol SAM to be patterned in the background of a second type of alkanethiol. Multiple printing steps can produce multiple patterns of molecules on a surface, but most patterns require the alignment of a stamp. Micromolding in capillaries (MIMIC) is a general method for depositing polymers, SAMs, and proteins in continuous patterns on a substrate, but MIMIC is unable to align multiple, discontinuous patterns. Three-dimensional networks of channels in PDMS can generate multiple, discontinuous patterns of proteins and cells, but the microfluidic networks require alignment in fabrication. Chen et al. have demonstrated an elegant technique using a multilevel PDMS stamp to print multiple, aligned regions of proteins. This technique involves several complicated steps (in fabrication of the stamp, in inking, and in printing or patterning).

A number of procedures for multicolor patterning have used photolithography. In one report, different fluorescent dyes were coupled in solution to a surface coated with bovine serum albumin (BSA) using irradiation with UV light through a photomask. Where light passed through the photomask, the fluorescent dye molecules were excited and produced radicals; fluorescent dye radical molecules coupled to BSA in regions defined mostly by the pattern of illumination. Although this method permitted multiple molecules to be patterned by using different wavelengths to excite different fluorescent dyes, alignment of individual patterns was not demonstrated, and the resolution of the features was limited by the diffusion of the fluorescent dyes. Another report described the use of diarylethene derivatives that undergo photoinduced structural rearrangements depending on the wavelength of light used. Two diarylethene derivatives were cast as a film and exposed sequentially through individual masks to UV or visible light.

The examples above show that many existing techniques require alignment of two (or more) features when fabricating either a photomask or a microfluidic device (e.g., photolithography, MIMIC) or alignment of a stamp when printing patterns of molecules (e.g., μCP, microcontact printing), in order to fabricate multiple patterns of molecules on a surface. There remains a general need in the art for improved methods of fabricating multiple patterns on a surface, without multiple steps of alignment.

SUMMARY OF THE INVENTION

This invention relates to the alteration of the molecules of a surface by photocleavage of the molecules. The subject matter of the present invention involves, in some cases, interrelated products, alternative solutions to a particular problem, and/or a plurality of different uses of one or more systems and/or articles.

One aspect of the invention provides a method. In one set of embodiments, the method includes acts of providing a surface, at least a portion of which comprises molecules attached thereon, exposing the surface to electromagnetic radiation, and altering the layer of molecules with the electromagnetic radiation to form a pattern comprising at least a first, second, and third region, where the first, second, and third regions differ from each other in at least one chemical and/or physical characteristic. In another set of embodiments, the method includes an act of reacting a photocleavable moiety to produce a SAM-forming species comprising the photocleavable moiety.

Another aspect of the invention provides a composition. The composition, according to one set of embodiments, includes a compound having a structure:

where X is an attachment moiety able to chemically bind a surface, Q comprises a photocleavable moiety, and R is a moiety connecting X and Q.

In another set of embodiments, the composition comprises a SAM-forming species comprising a photocleavable moiety, where the SAM-forming species is free from attachment to a surface.

Yet another aspect of the invention provides an article. According to one set of embodiments, the article comprises

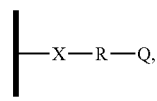

where l comprises a surface, X is an attachment moiety able to chemically bind a surface, Q comprises a photocleavable moiety, and R is a moiety connecting X and Q. In some cases,

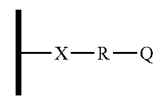

is not:

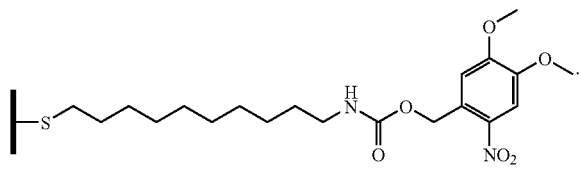

In another embodiment, the present invention is directed to a photomask comprising a first region that is transparent to light at a first wavelength within a first range, and opaque to other wavelengths of light not within this range; a second region that is transparent to light at a second wavelength within a second range, and opaque to other wavelengths of light not within this range, wherein the first and second wavelengths differ, and a third region that is opaque to wavelengths of light in at least the first and second ranges.

In another aspect, the present invention is directed to a method of making one or more of the embodiments described herein. In yet another aspect, the present invention is directed to a method of using one or more of the embodiments described herein. In still another aspect, the present invention is directed to a method of promoting one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 3 illustrates fabrication and characterization of a photomask.

FIG. 4 illustrates the preparation and immunolabeling of multiple, aligned SAMs.

FIG. 5A is a schematic illustration of the approach used to pattern multiple, aligned SAMs that resist the adsorption of proteins. Using the strategy outlined in FIG. 1B, a mixed SAM containing $HS(CH_2)_{11}EG_6NPOP(GRGD)$ and $HS(CH_2)_{11}EG_6OH$ was illuminate through an area-selective mask that transmits selectively light at 220 or 365 nm or blocks light at these wavelengths, to produce a bare gold (or oxidized gold) region, a SAM that terminates in primary amides, and a region containing the original SAM. FIG. 5B is an SPR sensor gram of the mixed SAMs for substrates that have not been exposed to light, that have been exposed to light at 365 nm, and that have been exposed to light at 220 nm. The original SAM, protected from exposure to light by the opaque, chromium area of the mask, remains resistant to the adsorption of fibrinogen (1 mg/mL, PBS buffer). After exposure to light at 365 nm, the SAM region that terminates in primary amides resists the adsorption of proteins, and after exposure to light at 220 nm, the gold (or oxidized gold) surface (the monolayer is cleaved entirely) is unable to resist the adsorption of proteins.

FIG. 7 shows the patterning two aligned SAMs that resist the adsorption of proteins and a third region that does not resist the adsorption of proteins.

DETAILED DESCRIPTION

Figure 1:
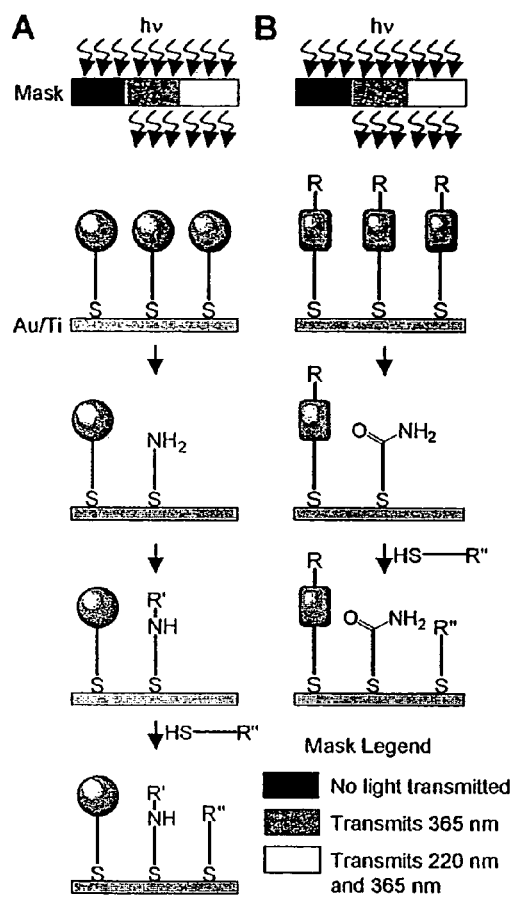
FIG. 1 is a schematic illustration showing patterning of a gold substrate with multiple, aligned SAMs using a photomask. Two methods are described: the photopatterning method described by process A (FIG. 1A) produces a SAM that terminates in amines after exposure to light at 365 nm, while the method described by process B (FIG. 1B) produces a SAM that terminates in primary amides after exposure to light at 365 nm. The method described by process B also permits the original SAM to present arbitrary functionality beyond the photocleavable linker. A new SAM can be formed in regions that are exposed to light at 220 nm in both approaches. R represents any group that can be coupled to a carboxylic acid, e.g., amine, alcohol, etc.; R' represents any group that contains a carboxylic acid, aldehyde, etc. that can be coupled to an amine; R" represents an arbitrary functionality that terminates with a thiol group. (Note: alkanethiol SAMs on gold substrates are tilted 30° to the normal and are shown here schematically without any tilt.)
Figure 1:
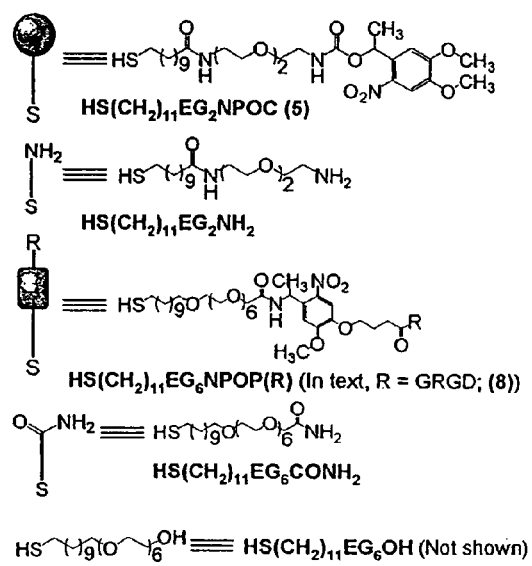

The present invention provides a series of methods, compositions, and articles for patterning a surface with multiple patterned regions that may differ from each other in at least one chemical and/or physical characteristic. Certain embodiments, as described in more detail below, and methods described herein can be utilized to fabricate surfaces having discreet, non-continuous patterns thereon that differ from each other with regard to their ability to interact with other substances and materials to which they are exposed. For instance, in certain embodiments, an article derived from practicing a method as described herein can result in a patterned surface characterized by at least first, second, and third regions that differ from each other in, for example, their hydrophobicity, ability to resist or promote binding of proteins, cytophilicity (i.e. ability to bind or resist binding of cells), and/or their ability to be etched or otherwise reacted by exposure to the solution containing a reactant, for example, an etching solution.

Various aspects of the invention provide methods, compositions, and articles for patterning a surface with molecules, for example multiple, aligned layers of molecules, by exposing the molecules to electromagnetic radiation. In certain embodiments, a single photomask acts as an area-selective filter for light at multiple wavelengths. A single set of exposures of multiple wavelengths through this photomask may make it possible to fabricate a pattern comprising discontinuous multiple regions, where the regions differ from each other in at least one chemical and/or physical property, without acts of alignment between the exposures. In certain embodiments, the surface includes molecules attached thereto that can be photocleaved upon exposure to a certain wavelength of radiation, thereby altering the chemical composition on at least a portion of the surface. In some embodiments, the molecules attached to the surface may include thiol moieties (e.g., as in alkanethiol), by which the molecule can become attached to the surface. In some embodiments, the molecules may be terminated at the unattached end with photocleavable groups. In other embodiments, a molecule that was photocleaved may be exposed to another molecule that binds to the photocleaved molecule. In certain cases, the molecules may be terminated at the unattached end with hydrophilic groups that may, for example, be resistant to the adsorption of proteins. In other cases, the molecules may be terminated at the unattached end with end groups that are not resistant to the adsorption of proteins. In certain embodiments, the techniques are used to pattern simultaneously two different regions that are resistant to the adsorption of proteins, and a third region that does not resist the adsorption of proteins.

As described in more detail below, articles comprising patterned surfaces as produced according to certain embodiments of the invention can be utilized in a very wide variety of applications requiring or benefiting from patterned surfaces including multiple regions comprising, in certain instances, non-continuous patterns having smallest feature sizes on the order of less than 1 millimeter, certain embodiments less than 100 microns, in other embodiments less than 10 microns, in yet other embodiments less than 1 micron, and in other embodiments on the scale of tens or hundreds of nanometers. The methods disclosed in more detail below can be utilized to form patterns on material surfaces comprised of an extremely wide variety of materials, as will become apparent to those of ordinary skill in the art. Also disclosed and provided herein are inventive photomask articles that can be, as described further below, utilized to form patterned layers or monolayers or self-assembled monolayers (SAMs) on material surfaces; to form patterns of inorganic materials on surfaces; to form patterns of organic and/or biological materials on surfaces; to form patterns on surfaces via contacting the surfaces with the material that chemically reacts with and/or creates/etches the material surface; etc. The ability of the present invention to, in certain embodiments, form patterned surfaces is, in certain respects, somewhat similar to known techniques of patterning surfaces via microstamping and soft lithography (see, e.g., International Patent Application No. PCT/US01/17246, filed May 25, 2001, entitled "Patterning of Surfaces Utilizing Microfluidic Stamps Including Three-Dimensionally Arrayed Channel Networks," by Anderson, et al., published as WO 01/89788 International Patent Application No. PCT/US2004/002498, filed Jan. 29, 2004, entitled "Alteration of Surface Affinities," by Jiang, et al., each incorporated herein by reference. A variety of such materials and applications is described in detail in U.S. Pat. Nos. 5,512,131; 5,620,850; 5,776,748; 5,900,160; 5,951,881; and 5,976,826, each of which is incorporated herein by reference).

In certain embodiments of the invention, a surface comprising a plurality of chemical chains including two or more different compositions can be formed. E.g., in the case of SAMs, a monolayer may comprise a first chemical chain and a second chemical chain having a different composition from the first chemical chain. This mixture of different compositions is referred to as a "mixed SAM". Mixed SAMs allow a surface to be tailored for a particular application. For example, some mixed SAMs show resistance to protein adsorption when present in an amount as low as 25% of the total of chemical chains. Of course, three or more different SAM types can be readily contemplated.

As will become more apparent in the discussion below, certain embodiments of the inventive methods and articles provided according to the present invention can provide several advantages over traditional microstamping and other soft lithography techniques. For example, certain methods disclosed herein have the ability to form patterns comprising at least three distinct regions, each of which is characterized by a different set of chemical and/or physical properties, for example, in certain embodiments, by the presence on a surface of different molecular species. Typical soft lithography techniques are capable of patterning only two types of molecules on the surface, especially for applications wherein the patterned molecules comprise aligned molecules, such as SAMs. In certain embodiments, wherein pattern formation is effected via exposing a surface of an article to electromagnetic radiation, such as light, through a wave length-selective patterned photomask, the inventive methods can provide for the formation of patterns comprising multiple discreet regions without the need for realignment of a photomask between exposures of the surface to the electromagnetic radiation, and, in certain instances, can provide for the formation of each of the discreet regions of the pattern simultaneously with a single exposure to the electromagnetic radiation. As previously eluded to above, articles comprising patterned surfaces such as can be fabricated according to certain embodiments of the present invention may be utilized in a wide variety of applications, for example, for use in biochemical assays, as microarrays (e.g. for proteomics and/or geonomics); as gene-chips; as MEMS devices; or as substrates for use in applications involving differential etching chemistry.

In one particular set of embodiments, the inventive articles provided according to certain embodiments of the inventions, because it is possible to create arbitrarily complex patterns comprising a large number of patterned regions containing different patterned molecular species, articles divided according to certain of the inventive methods potentially having extremely wide range of use for cellular manipulation, drug screening (e.g. utilizing cell-based drug screening assays); studies of cell-signaling; studies of cell morphology and architecture as it relates to function; etc. For example, in one exemplary application, the inventive articles can provide a patterned surface having the ability to bind to cells and/or proteins to different degrees for different regions. In such an example, proteins, for example, can be selectively patterned onto a surface which are adhesive to cells, non-adhesive to cells, or selectively adhesive to certain cells while non-adhesive to other cells. By forming patterns with such proteins, or other cell-binding molecules, complex patterns of one cell type or a variety of cell types can be selectively patterned onto surfaces for various applications, for example, for forming biosensors or performing drug screening tests. Using the methods disclosed below, it is possible to pattern a large number of different cell types, each separated from each other and arranged in a patterned array format. Such patterning can be accomplished, according to certain embodiments of the invention, by, for example, coating a surface with a surface coating, for example, a SAM, in certain embodiments comprising a SAM-forming molecule that is bound to the surface that includes as part of its structure a photocleavable moiety, exposing the surface, for example, through a photomask, to electromagnetic radiation, and altering the layer of molecules on the surface with the electromagnetic radiation to form a pattern comprising multiple regions, in certain embodiments at least first, second, and third regions, that differ from each other in their ability to adhere proteins and/or cells. Such ability to form patterns comprising arrays of regions, with each region including a particular cell, protein, molecular species type or mixture of cell, protein, molecular species types, can enable the creation of material surfaces for use of biosensors or drug screening devices having cells or other materials patterned thereon that can be easily and readily identified by their spatial locations on the surface.

As mentioned above and as described in much more detail below, certain embodiments of the inventive methods can form an article having a patterned surface by exposing a surface which comprises a layer of molecules attached thereon to electromagnetic radiation, for example through a wavelength and area selective photomask, such that the layer of molecules in different regions are differentially altered by the electromagnetic radiation to form a pattern comprising discreet regions each having a different chemical property, for example characterized by a different molecular species attached to the surface in such region. In certain such embodiments, the layer of molecules attached to the surface that are modified via exposure to the electromagnetic radiation are formed via attachment to the surface of molecular species, such as SAM-forming species, which have a structure comprising a moiety able to attach to a particular surface or substrate (e.g. a thiol moiety for metallic surfaces such as gold, silver, copper, or other noble metals, a saline moiety for attachment to silicon atom-containing surfaces such as glass, or a wide variety of other attachment moieties as mentioned below), connected, for example via a linker such as an alkyl moiety, to a photocleavable moiety, which is able to be cleaved by exposure to electromagnetic radiation, such as light, at a wavelength and/or intensity that is not able to cleave other bonds within the molecule attached to the surface. A wide variety of such molecular species including photocleavable moieties, for example SAM-forming species are described in much more detail below.

In one aspect of the present invention, inventive SAM-forming species are provided, as described in much more detail below, which comprise a photocleavable moiety. Advantageously, and according to certain embodiments of the invention, such SAM-forming species are synthesized in solution and free from attachment to a surface. Such SAM-forming species may therein be deposited onto surfaces of articles and attached thereto via appropriate selection of an attachment moiety of the SAM-forming species. In certain embodiments, the inventive SAM-forming species comprise alkanethiols comprising one or more photocleavable moieties (see FIGS. 1, 4, 5 and associated discussion below), which are well suited for attachment to gold-containing surfaces. It is known that that thiol-gold bond connecting alkanethiols to the gold-containing surface can be ruptured, freeing the alkanethiol from the surface, via exposure to light at about 220 nm. Certain aspects of the present invention provide the provision of alkanethiol species attached to a gold surface that include a photocleavable moiety, for example, any one of a variety of photocleavable amine-protecting groups or photocleavable linkers known to those of skill in the art and described in greater detail below, which have the ability to be cleaved at wavelengths that are greater than the 220 nm able to cleave the gold thiol bond and at wavelengths that are unable to cause cleavage of other bonds within the molecule. Accordingly; in such embodiments, by exposing a surface coated with the SAM comprising such photocleavable alkanethiols, differentially pattern regions can be formed by exposing such surface to light through a photomask (see, for example, FIGS. 1A and 1B) having first regions (left most regions in the Figures) that are essentially opaque to light at all relevant wavelengths from a source of light, second pattern regions (gray central regions in the Figures) that are configured to transmit light at a wavelength able to cleave the photocleavable moiety (e.g. 365 nm for the photocleavable moieties illustrated in FIG. 1) but not cleave the sulfur gold surface bond and release the entire alkanethiol from the surface, and third regions (white regions in the Figures) that are configured to transmit light at a wavelength that is able to cleave the entire alkanethiol from the surface. Although photocleavable groups having sensitivity to light at 365 nm are exemplified in FIG. 1 and alkanethiols have been used in conjunction with gold surfaces wherein association of the alkanethiols from the surface can be effected by exposure to light at 220 nm., it should be understood that in other embodiments, photocleavable moieties and/or surface-attachment moiety combinations can be chosen such that they are sensitive to cleavage at other wavelengths of light, and/or other types, wavelengths, intensities, etc. of electromagnetic radiation. A variety of such alternative materials could be envisioned by those of ordinary skill in the art in view of the present teachings and applied using no more than routine testing and experimentation.

As illustrated in FIG. 1, exposure of a surface coated with photocleavable alkanethiols, such as those discussed above, upon exposure to light at the first and second wavelengths through the photomask is characterized by a pattern comprising three discreet regions having a surface which, attached thereto are different molecular species, or no molecular species. In the embodiment illustrated in FIG. 1A, for example, exposure to light at 365 nm and 220 nm through the photomask results in a first region (left), which has not exposed to light at either 365 or 220 nm and which comprises attached thereto the complete alkanethiol originally present on the surface; second regions (center) exposed to light at 365 nm, but not 220 nm, which comprise attached thereto a cleavage product of the originally present photocleavable SAM-forming species which, in the illustrated embodiment, provides a terminal group comprising a reactive functionality (a amine group is illustrated) and is terminus. Of course, in other embodiments, determines of the cleaved molecular species could comprise any of a wide variety of other functionalities including, but not limited, carboxylic acids, alcohols, aldehydes, amides (e.g. see FIG. 5); and a third region (right) exposed to light at 220 nm from which the entire alkanethiol moiety has been cleaved exposing the underlying surface of the substrate. If desired, in certain embodiments as illustrated in FIG. 1, after exposure to electromagnetic radiation resulting in the differential pattern formation, the surface of the article may be exposed to and reacted with other species that are able to bind to one or more of the patterned regions (e.g., are able to react with the terminal functionality of the cleaved photocleavable alkanethiol or are able to react with the exposed substrate surface). In other embodiments, more complex patterns could be created utilizing additional regions of attachment of molecular species having differing photocleavable moieties and/or attachment moieties sensitive to wavelengths and/or intensities of electromagnetic radiation of differing values. In yet other embodiments, additional pattern formation flexibility could be achieved by providing coatings, for example, SAMs comprising photocleavable molecular species having more than one photocleavable moiety present within the structure, which are each able to be cleaved at different wavelengths, intensities, etc. In certain embodiments of the inventive methods involving patterning surfaces having attached thereto via a photosensitive attachment moiety molecular species comprising a photocleaveable group, such as, for example, a photocleavable SAM such as a photocleavable alkanethiol, it can be advantageous to utilize photocleaveable molecular species including a photocleavable moiety that is able to be cleaved with light of a wavelength exceeding the wavelength required to cleave the bond directly attaching the molecular species to the substrate surface. For example, in the case of alkanethiols in which the sulfur-surface bond is typically able to be cleaved utilizing light at a wavelength of about 220 nm, it is preferable to include a photocleavable moiety in such a molecular species that is able to be cleaved with light having a first wavelength greater than this, for example at least about 250 nm. In addition, because at wavelengths below about 200 nm carbon-carbon and other intermolecular bonds are often able to be cleaved more or less at random, it can be advantageous to utilize an attachment moiety in a molecular species to be coded onto a surface that is able to be cleaved at a wavelength less than the wavelength able to cleave the photocleavable moiety but greater than the wavelength able to indiscriminately rupture molecular bonds. Such election can increase the selectivity of bond rupture and result in more predictable and "clean" cleavage of molecular species from a surface. For example, in certain embodiments, it can be advantageous to utilize a molecular species, such as SAM-forming species, that becomes bound to a surface via a bond that is able to be cleaved with light having a wavelength of at least about 200 nm, but less than the wavelength of any other photocleavable moiety present within the molecular species. In certain embodiments, it can be advantageous to utilize SAM-forming species for attachment to surfaces to be patterned that do not require presence of scavenger molecules during photocleavage. A variety of such species and photocleavable moieties are known in the art and are described in more detail below in the context of the appended examples. In general, described in much greater detail below, are a wide variety of useful or potentially useful molecular species; such as SAM-forming molecular species, such as alkanethiols, that are useful for practicing the above-described embodiments of the invention.

As discussed above, certain embodiments of the present invention provide patterning methods and patterned articles that can have certain advantages over those produced by conventional patterning techniques, such as soft lithography. For example, in certain embodiments of the inventive methods for forming pattern surfaces via exposure of a surface to electromagnetic radiations through a photomask, it is not necessary to directly contact the surface with the photomask. By contrast, micro-stamping and other micro-contact soft lithography techniques generally require contact of the stamping surface with a surface to be patterned. Avoiding such contact, as can be accomplished via practicing certain aspects of the present invention may be able to produce pattern regions having greater uniformity, improved surface coverage, lack of contamination caused by exposure to the stamp material, etc. In addition, because, in certain embodiment, the invention provides for formation of patterns via exposure to electromagnetic radiation via a rigid photomask, it may be possible to provide more consistent shapes and/or dimensions for pattern features and/or to achieve greater resolution and small feature size. For example, certain embodiments, at least one region of a pattern formed according to a method of the present invention via exposure of a surface to electromagnetic radiation resulting in modification of the surface to produce a pattern, a region of the pattern being characterized by having a smaller cross-sectional dimension not exceeding about 100 microns, and other embodiments not exceeding about 90 microns, 80 microns, 70 microns, 60 microns, 50 microns, 40 microns, 30 microns, 20 microns, 10 microns, 5 microns, 1 micron, 500 nm, 400 nm, or less. One aspect of the invention also provides the novel photomask article figure to be utilized in the context of certain embodiments of the inventive methods. The inventive photomask comprises a new type of photo lithography mask that is configured to provide different regions having the ability to transmit or block selective wavelength(s) of light within the ultraviolet spectrum, which typically includes those wavelengths of light able to cleave chemical bonds, such as those present in photocleavable moieties and/or attachment moieties connected to a surface according to certain embodiments of the invention. Fabrication methods and further characteristics of the inventive photomask according to certain embodiments of the invention are discussed in more detail below and presented in Example 2.

As described herein, in some aspects of the invention, the application of light (photons) to at least a portion of a substrate according to certain embodiments of the invention can cause at least a portion of a molecule attached to at least a portion of the substrate to be cleaved from the molecule ("photocleaved"). A portion of the molecule that reacts with light to cause cleavage of the molecule is a "photocleavable moiety." In some cases, the light has a wavelength selected to cleave a portion of the photocleavable moiety (e.g., a covalent bond) but insufficient to cleave other covalent bonds in the molecule. For example, the light may have a wavelength of about 365 nm or about 220 nm. In one aspect of the invention, the molecule attached to the substrate forms part of a self-assembled monolayer.

For example, in certain embodiments, the substrate may be exposed to light selected to cause cleavage of a portion of a photocleavable molecule. The substrate may be exposed to such light for at least about 5 seconds, at least about 10 seconds, at least about 15 seconds, at least about 30 seconds, or at least about 1 minute or more in some cases. In certain embodiments, the substrate may be exposed to such light for less than about 10 minutes, in some cases in less than about 5 minutes, and in other cases in less than about 2 minutes. In some cases, the substrate may be exposed to such light for between about 5 seconds and about 3 minutes, in other cases between about 10 seconds and about 2 minutes, in other cases between about 30 seconds and about 1 minute, and in still other cases between about 10 seconds and about 1 minute.

An "attached" molecule, as used herein, refers to one that is sufficiently immobilized with respect to a surface or other entity such that it will not detach under typical conditions of use (i.e., by fluid movement or thermal energy), without exposure to light selected to cause detachment of the molecule or a portion thereof.

The molecules attached to the substrate may be hydrophilic or hydrophobic in some cases, or the molecules may have an affinity to another entity, as described above. In some cases, the substrate may include more than one type of molecule thereon that can be photocleaved. For example, the substrate may include a first type of molecule that is photocleaved the substrate is exposed to light having a first frequency, and a second type of molecule that does not detach when the substrate is exposed to the light having a first frequency, but is able to be photocleaved when the substrate is exposed to a second frequency.

The present invention describes, in another set of embodiments, a method for patterning a surface comprising at least a first, second, and third region of attached molecules, which differ in either chemical and/or physical property, using one photomask and one set of exposures to light at different wavelengths, but without alignment of photomasks (FIG. 1). In some embodiments, the regions of the first, second, and third regions, or any combination thereof, may be discontinuous. In some cases, the molecules attached to the substrate may be photocleaved upon exposure to a certain wavelength of radiation, thereby leaving at least a portion of a molecular species on the surface. In other cases, the molecules attached to the substrate may be photocleaved entirely such that the bare surface is exposed.

In some cases, bonds can be photocleaved selectively in different regions of a SAM using one or more masks, which may be able to transmit light at some wavelengths and/or regions, and at least partially inhibit the transmission of light at other wavelengths and/or regions. For example, in some cases, the mask may include holes, and/or the mask may include regions which selectively allow the transmission of light having certain frequencies. A specific, non-limiting example, is an area- and wavelength-selective mask (i.e., a photomask that transmits different wavelengths in different areas). In some embodiments, the photomask is selective for transmitting light of about 365 nm through the mask, and generally opaque to light of other wavelengths. In another embodiment, the photomask is selective for transmitting light of about 220 nm through the mask, and generally opaque to light of other wavelengths. In yet another embodiment, the photomask is selective for transmitting light of about 365 nm and about 220 nm through the mask, and generally opaque to light of other wavelengths. In still other embodiments, the transmission of light through the photomask is not limited to these wavelengths, but can include any number and combination of patterns and wavelength-selective regions, as is described herein.

Different wavelengths of light that pass through the photomask allow different points of cleavage of a molecule species. In certain embodiments, a pattern may be formed via cleavage of at least a portion of a molecule species attached on the surface within a first region. In another embodiment, the point of cleavage of a molecular species attached on a surface may be different from a point of cleavage of the molecular species attached on the surface within the second region. For example, in one embodiment, light of 365 nm cleaves an amine-protecting group; in another embodiment, light at 220 nm removes the entire SAM (regardless of functionality) from the surface and produces a region of unprotected gold. In some cases, a different SAM can be formed in regions that were exposed to light at 220 nm upon incubation with a different alkanethiol. In some cases, other entities such as molecules, proteins, or particles (such as nanoparticles) can react or bind to the surface by exposing the molecule to particular regions of the surface. These entities may be presented to surface in any suitable form, such as in a solution, gas, or solid. SAMs in regions that are protected from exposure to light at 220 and 365 nm remains intact, but may also undergo reaction or binding to the suitable entities described herein.

Figure 3A:
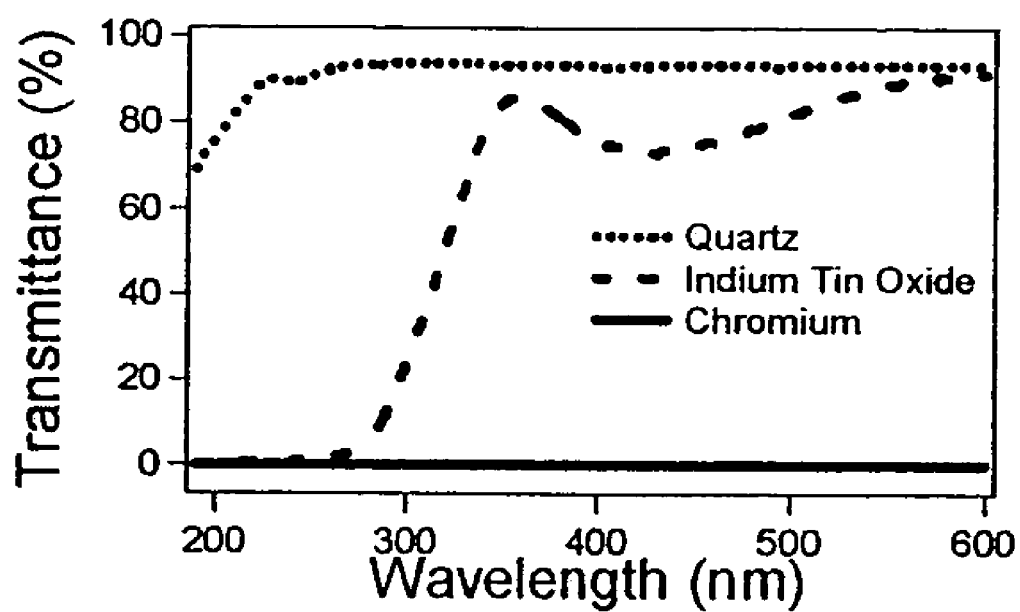
FIG. 3A shows the transmission spectra of each component used in the mask. Chromium is sufficiently opaque to prevent significant transmission of light at 220 or 365 nm. Indium tin oxide is sufficiently transparent to light at 365 nm and opaque to light at 220 nm to filter deep UV wavelengths during exposure. Quartz is transparent to light at all wavelengths used in this study.

As a non-limiting example, a microfabricated mask can be used as an area- and wavelength-selective filter in the patterning multiple, aligned SAMs. The fabrication of the photomask described herein may be made using any methods or techniques, or any materials, that are available to those skilled in the art. For example, a mask can be fabricated by using a commercially available quartz substrate coated with indium tin oxide (ITO) as the initial substrate. ITO blocks light at 220 nm; quartz transmits light at 220 nm (FIG. 3A). Using electron-beam metal evaporation, films of either chromium or gold can be deposited on the ITO to block light at 365 nm, in addition to light at 220 nm. It should be understood that other substrates can be used, and other techniques to deposit metals or other materials on the substrate may be used to achieve the same or similar results. In addition, other metals or materials may be deposited on the substrate to block or transmit light at other wavelengths, and can be used for achieving the same or similar purposes and/or results.

Figure 4A:
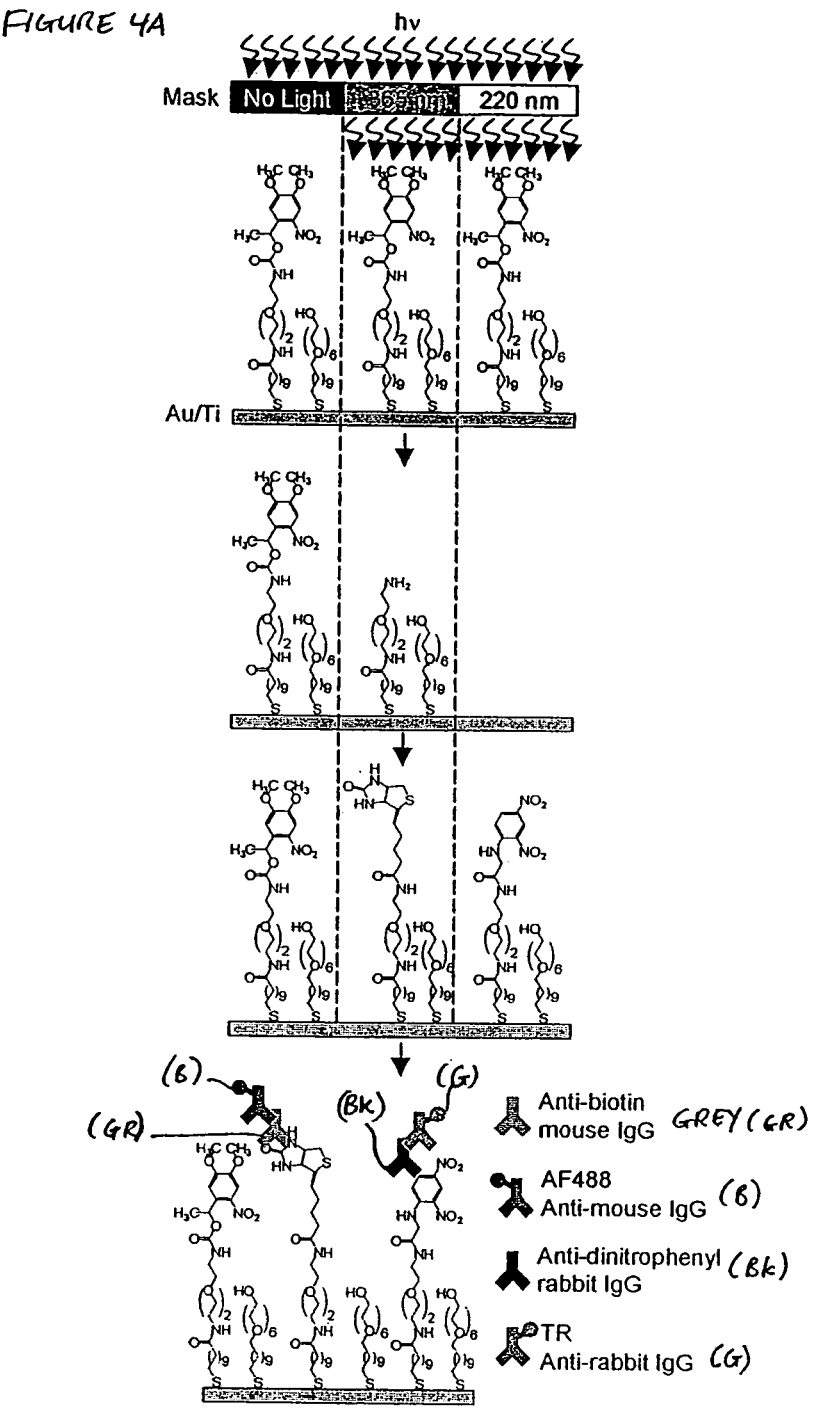
FIG. 4A is a schematic illustration of patterning multiple, aligned SAMs using a photomask. Using the strategy outlined in FIG. 1A, a mixed SAM containing $HS(CH_2)_{11}EG_2NPOC$ and $HS(CH_2)_{11}EG_6OH$ was illuminated through an area-selective mask that transmitted light either at 220 or 365 nm only or that blocked light at all wavelengths, to produce a region containing the original SAM, a SAM that terminated in primary amines, and a region of bare gold. (or oxidized gold). (+)-biotin N-hydroxysuccinimide ester was allowed to react with the primary amines and also formed a new SAM composed of $HS(CH_2)_{11}EG_2DNP$ and $HS(CH_2)_{11}EG_6OH$ on the exposed gold. SAMs were labeled using anti-biotin mouse IgG (followed by fluorescently labeled anti-mouse IgG) and anti-DNP rabbit IgG (followed by fluorescently labeled anti-rabbit IgG).
Figure 4B:
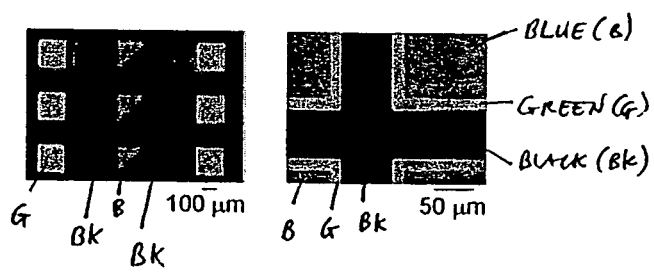
FIG. 4B are fluorescence images of patterns of multiple, aligned SAMs.

The feature size wherein at least one region of the pattern was characterized by a smallest cross-sectional dimension, produced by the methods herein, may be on the order of less than about 100 microns, less than about 10 microns, or less than about 1 micron (e.g., FIG. 4B). The resolution of the features typically reflects the method used to fabricate the regions of the mask that transmitted light. In some embodiments, these regions can be fabricated by wet-etching ITO to expose quartz. In other embodiments, alternative fabrication processes may include dry-etching (e.g., deep reactive ion etching) or other methods of producing a mask having similar results.

In some embodiments, a photocleavable linker was used to pattern two aligned SAMs that are resistant to the adsorption of proteins and a third region that does not resist the adsorption of proteins.

Certain embodiments of the invention involve surfaces with SAMs attached thereon. As used herein, the term "self-assembled monolayer" (SAM) refers to a relatively ordered assembly of molecules attached on a surface, in which the molecules are oriented approximately parallel to each other and roughly perpendicular to the surface. The molecules may be attached to the surface through a bond, for example, a metal-sulfur bond.

A SAM-forming molecule may be attached to the substrate by any of a wide variety of suitable mechanisms known in the art that result in stable SAM formation on the substrate. For example, in one series of embodiments, the substrate and SAM-forming compound are selected such that the SAM-forming compound terminates at a first end in a functional group that attaches to, and typically binds to, a surface of the substrate. As used herein, the terminology "end" of a compound includes both the physical terminus of a molecule as well as any portion of a molecule available for forming a bond or other attachment with the substrate in a way that the compound can form a SAM on the substrate. A "bond," as used herein in this context, broadly refers to any physical and/or chemical attractive interaction between a first entity, such as a molecule, and another entity, such as the surface of the substrate, where the force of the attractive interaction is of the magnitude of chemical bond forces and is generally sufficient to allow the first entity to become immobilized with respect to the other entity. Some examples of such "bonds" include, without limitation, a covalent bond, a coordinated bond, chemisorption (e.g., a metal-sulfur bond), hydrogen bonding, and the like. The affinity may also be characterized as cytophilic and/or cytophobic in nature, as further described below.

The compound may comprise, for example, a molecule having first and second terminal ends, separated by a spacer portion, the first terminal end comprising a first functional group selected to bond to the surface of the substrate, and the second terminal end optionally including a second functional group selected to provide a SAM on the substrate that has a desirable functionality, and/or a functionality that can be reacted to produce a desirable functionality, as further described below. The spacer portion of the molecule may be selected to provide a particular thickness of the resultant SAM, and/or to facilitate SAM formation. Although SAMs of the present invention may vary in thickness, e.g., as further described below, SAMs having a thickness of less than about 50 Angstroms, less than about 30 Angstroms or less than about 15 Angstroms may be particularly useful in certain instances. These dimensions are generally dictated by the selection of the SAM-forming compound and in particular the spacer portion thereof, and can be readily selected and/or prepared by those of ordinary skill in the art.

The SAM-forming molecule, in some embodiments, may also include a spacer portion that interacts with neighboring molecules in the monolayer to form a relatively ordered array. The spacer functionality of the SAM-forming compound may connect a functional group able to bind or otherwise attach to the substrate with a functional group at a second end of the molecule, as further described below. Alternately, a portion of the spacer may form the functional group. Any spacer that does not substantially and undesirably disrupt SAM packing is potentially suitable. The spacer may, in specific embodiments, be, for example, polar; non-polar; halogenated or, in particular, fluorinated; positively charged; negatively charged; or uncharged. As additional examples, a saturated or unsaturated, linear or branched alkyl, aryl, or other hydrocarbon spacer may be used in certain embodiments of the SAM-forming compound.

A variety of lengths of SAM-forming compounds can potentially be employed in the present invention. If two or more different SAM-forming compounds are used, it is sometimes advantageous that these species have similar lengths. However, in certain embodiments, for example when a two or more step process is used, in which a first SAM is provided on a surface and at least a second SAM is provided on the surface, the various SAMs being continuous or noncontinuous, it may be advantageous in some circumstances to select molecular species for the formation of the various SAMs that have different lengths. For example, if the SAM initially formed has a first molecular length and the SAM subsequently derivatized to the surface has a second molecular length greater than that of the first molecular length, a continuous SAM having a plurality of "wells" may result. These wells are the result of the first SAM being surrounded by the second SAM having a longer chain length. Such wells may be advantageously fabricated according to certain embodiments, for example, when it is desirable to add greater lateral stability to particular biological materials, such as cells, which have been captured in the wells. Such wells may also form the basis for reaction vessels.

Methods that can be used to form a SAM are well known and are described in, for example, U.S. Pat. No. 5,620,850, which is hereby incorporated by reference. See also, for example, Laibinis, P. E., Hickman, J., Wrighton, M. S., Whitesides, G. M., *Science*, 245:845, 1989; Bain, C., Evall, J., Whitesides, G. M., *J. Am. Chem. Soc.*, 111:7155-7164, 1989; Bain, C., Whitesides, G. M., *J. Am. Chem. Soc.*, 111:7164-7175, 1989, each of which is incorporated herein by reference. In some cases, the SAM can be made up of SAM-forming species that form SAMs on surfaces, and/or those species in combination with other species able to participate in a SAM. In some embodiments, some of the species that participate in the SAM include a functionality or group able to bind, optionally covalently, to a surface, such as a thiol functionality which will chemisorb to a gold surface.

The SAM-forming compound may terminate in a second end, generally opposite to the end bearing the functional group selected to bind to the surface material. The second end can comprise any of a variety of functionalities. For example, in one embodiment of the invention, at least some of the SAM-forming molecules forming a SAM have a structure:

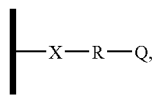

where I comprises a surface, X is an attachment moiety able to chemically bind a surface, Q comprises a photocleavable moiety, and R is a moiety connecting X and Q. As discussed above, the bond connecting S to the substrate may be any bond capable of immobilizing the SAM-forming molecule to the surface, for example, a chemisorption bond such as a gold-sulfur bond. Q may also comprise other moieties, for example alkyl moieties, or functional moieties such as those described herein.

In one embodiment,

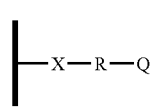

is not:

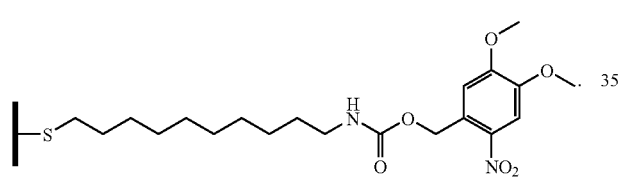

In one aspect of the invention, the compound to be attached to a surface of a substrate may have a structure:

X—R-Q, where X is an attachment moiety able to chemically bind a surface, Q comprises a photocleavable moiety, and R is a moiety connecting X and Q. An "attachment moiety" is a moiety of a molecule that can interact with a surface (e.g., through covalent binding) to attach the molecule to the surface. An example of an attachment moiety is a thiol functionality (i.e., —SH), which may react covalently with a surface to produce a sulfur-substrate bond, for example, a gold-sulfur bond if the surface comprises gold). Other examples of attachment moieties are disclosed herein.

Examples of photocleavable moieties are known to those of ordinary skill in the art. In one set of embodiments, a photocleavable moiety is cleaved from the compound upon exposure of the compound to light comprising a wavelength of at least about 250 nm, at least about 325 nm, or any other wavelength(s) disclosed herein. In some cases, the photocleavable moiety may comprise an aromatic group, and in certain cases, the photocleavable moiety may comprise an aromatic group. In one embodiment, the photocleavable moiety comprises a structure:

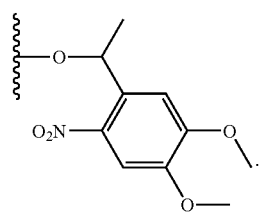

where each of $Z^1$, $Z^2$, $Z^3$, $Z^4$, $Z^5$, and $Z^6$ independently is one of —H, a halogen, an alkyl such as methyl or ethyl, —OH, or an alkoxy such as methoxy. As a non-limiting example, in one embodiment, at least two of $Z^1$, $Z^2$, $Z^3$, $Z^4$, or $Z^5$ independently is an alkoxy such as methoxy, with the remainder of $Z^1$, $Z^2$, $Z^3$, $Z^4$, or $Z^5$ being —H or an alkyl such as methyl or ethyl, for example, as in a structure:

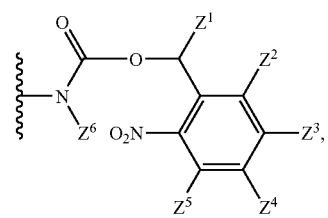

The above-described photocleavable moiety may be connected to the rest of the molecule by an amide bond, e.g.,:

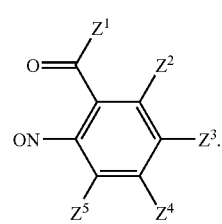

where $Z^6$ is independently one of —H, a halogen, an alkyl, —OH, or an alkoxy, and, upon photocleavage, the photocleavable moiety may no longer be covalently attached to the rest of the molecule, i.e., upon photocleavage, the photocleavable moiety forms a leaving group, for example comprising a structure:

Q may also contain other moieties, for example, functional groups such as those further described below, amino acids, additional alkyl moieties, ethylene glycol units, propylene glycol units, carbonyls, amide bonds, amines, alkoxys, halogens, etc. For instance, in one embodiment, Q may have a structure:

where $Q^1$ is photocleavable and $R^1$ comprises an alkyl moiety.

In the discussions above, R is a moiety connecting X and Q. In some cases, R defines a series of atoms interconnected by covalent bonds between X and Q. R may include, for example, one or more alkyls, ethylene glycol units, propylene glycol units, carbonyls, alkoxys, halogens, etc. In some cases, R is not photocleavable.

In some embodiments, the systems and methods described herein use a polyfunctional alkanethiol that forms a SAM on a gold substrate and that presents two types of photocleavable bonds: an o-nitrobenzyl amine-protecting group that cleaves on exposure to light at 365 nm and a thiolate bond (Au—S) that cleaves on exposure to light at 220 nm. It should be understood, however, that other similar embodiments having polyfunctional photocleavable bonds at the same or different wavelengths may be used for achieving the same or similar purposes and/or results. In addition, other suitable substrates for SAMs such as Ag, Pt, Pd, and/or Cu may be used. In cases where species other than alkanthiols are used to form one or multiple layers of molecules on the surface, such as silanes, other suitable substrates such as glass and silicon may be employed.

In some embodiments, a photocleavable molecule that does not require the use of scavengers, such as solution-phase scavengers, can be used. For example, photocleavable amine-protecting groups such as 1-(3,4-(methylenedioxy)-6-nitrophenyl) ethylchloroformate (MeNPOC, $(CH_3O)_2C_6H_2NO_2CH(CH_3)OCOCl$), which cleaves quantitatively on photolysis using near-UV light (365 nm) and regenerates the amines (FIG. 1A), can be used. MeNPOC does not necessarily require the use of solution-phase scavengers. In some embodiments, a surface comprising MeNPOC may be further modified: the amines generated by deprotection can be modified using traditional solid-phase synthetic methods, or any other methods familiar with those of ordinary skill in the art.

In another embodiment, photocleavable linkers, such as 3-[5-(1-amino-ethyl)-2-methoxy-4-nitro-phenoxy]-propionic acid (NPOP, $H_2NCH(CH_3)C_6H_2(OCH_3)O(CH_2)_3CO_2H$), can be used. NPOP may permit the alkanethiol to include functional groups beyond the photosensitive group (FIG. 1B). The o-nitrobenzyl component can be modified to present another chemical functionality, either before or after photopatterning. Thus, as an example, a SAM that contains NPOP and that is exposed to light at 365 nm can be converted to a SAM that terminates in primary amides, which can be functionalized further (e.g., by reduction to amines with lithium aluminum hydride).

Alkyl or aliphatic groups useful or potentially useful for practicing the invention can contain any of a wide number of carbon atoms, for example, between 1 and 30 carbon atoms, between 1 and 20 carbon atoms, between 1 and 15 carbon atoms, or between 1 and 10 carbon atoms. In some embodiments, the alkyl may have at least 2 carbon atoms, in other embodiments at least 3 carbon atoms, in other embodiments at least 11 carbon atoms, in other embodiments at least 13 carbon atoms, and in other embodiments at least 18 carbon atoms. In certain embodiments, the alkyl may have between 11 and 18 carbon atoms inclusive or between 13 and 18 carbon atoms inclusive. In some cases, the alkyl may comprise a chain of 1, 2, 3, 4, 5, 6, 7, 8, 9, 10, 11, 12, 13, 14, or 15 or more carbon atoms. In one set of embodiments, the alkyl may be an undecyl, a dodecyl, a tridecyl, a tetradecyl, a pentadecyl, a hexadecyl, a heptadecyl, or a octadecyl moiety. The carbon atoms may be arranged in any permissible configuration within the alkyl moiety, for example, as a straight chain or a branched chain (including multiple branches). The alkyl moiety may contain only single bonds, or alternatively, may contain one or more double or triple bonds within its structure, for example, as in an alkene, an alkyne, an alkadiene, an alkadiyne, an alkenyne, etc. The alkyl moiety may also contain one or more substituents in some embodiments. For example, in certain embodiments, the alkyl group may contain a halogen, an alkoxy (e.g., methoxy or ethoxy), an amine (e.g., a primary, secondary, or tertiary amine), or a hydroxide as a substituent. If more than one substituent is present, then the substituents may be the same as or different from each other. In some cases, the carbon atoms may be interspersed with other atoms, for example, oxygen or nitrogen atoms. For example, the alkyl moiety may comprise an amide bond, or one or more alkoxy moieties. In some cases, the alkyl may contain one or more rings (e.g., cycloalkyls, aromatic rings, etc.).

The term "halogen," or equivalently, "halogen atom," is given its ordinary meaning as used in the field of chemistry: The halogens include fluorine, chlorine, bromine, iodine, and astatine, and may have any charge state and/or electronic configuration. In some cases, the halogen atoms include one or more of fluorine, chlorine, bromine, or iodine. In certain embodiments, the halogen atoms found within the compositions of the invention are fluorine, chlorine, and bromine; fluorine and chlorine; chlorine and bromine, or a single type of halogen atom.

An "aromatic" moiety is given its ordinary meaning as used in the art, i.e., a moiety having at least one ring in which some electrons are delocalized in the ring. For instance, the aromatic moiety may include a benzene moiety, a naphthalenyl moiety, an anthracenyl moiety, a pyridinyl moiety, a furanyl moiety, etc. In one embodiment, the aromatic moiety is a nitroaromatic moiety, i.e., an aromatic moiety comprising —$NO_2$.

In one set of embodiments, the alkyl may comprise polyethylene glycol ("PEG") and/or polypropylene glycol ("PPG") moieties, e.g., moieties having the general formula —$OCH_2CH_2)_n$— or —$(OCH_2CH_2CH_2)_n$—, respectively, where n is any number of repeat units that gives the SAM-forming molecule, when the SAM-forming molecule is formed into a SAM on a surface, a desirable surface characteristic, such as cytophobicity or biophobicity, as those terms are further defined herein. The actual number of repeat units in the SAM-forming molecules utilized can be determined by those of ordinary skill in the art, depending on the specific application, using routine experimentation. In certain embodiments, the functional group may include various combinations of polyethylene glycol and polypropylene glycol repeat units (including block and/or alternating combinations). In some cases, some or all of the polyethylene glycol and/or polypropylene glycol repeat units are substantially unmodified, i.e., the units have the general formula —$(OCH_2CH_2)_n$—OH and/or —$(OCH_2CH_2CH_2)_n$—OH, respectively. In certain cases each n can independently be between 1 and 20 inclusive, in certain embodiments between 1 and 10 inclusive, and in certain embodiments between 1 and 8 inclusive. For instance, n may be at least 1, 2, 3, 4, 5, 6, 7, 8, or 9.

In some cases, the molecule may comprise a functional group that confers a specific property to the SAM-forming molecule. That is, the compound may include a functionality that, when the compound forms a SAM on the surface material, is able to confer upper the surface a specific property, such as an affinity for a particular entity or entities. For example, in certain non-limiting embodiments, the molecule can comprise a cytophilic moiety, a cytophobic moiety, a biophilic moiety, a biophobic moiety, a hydrophilic moiety, a hydrophobic moiety, a chelating group, an antibody, a peptide or protein sequence, a nucleic acid sequence, an affinity tag (e.g., a member of a biotin/avidin or biotin/streptavidin binding pair), or a moiety that selectively binds various biological, biochemical, or other chemical species, etc.

In some embodiments, the molecule may include, for example, ionic, nonionic, polar, nonpolar, halogenated, alkyl, or aryl. A non-limiting, exemplary list of functional groups that Z could comprise include: —OH, —CONH—, —CONHCO—, —NH$_2$, —NH—, —COOH, —COOR, —CSNH—, —NO$_2^-$, —SO$_2^-$, —RCOR—, —RCSR—, —RSR, —ROR—, —PO$_4^{-3}$, —OSO$_3^{-2}$, —COO$^-$, —SOO$^-$, —RSOR—, —CONR$_2$, —CH$_3$, —PO$_3$H$^-$, -2-imidazole, —N(CH$_3$)$_2$, —NR$_2$, —PO$_3$H$_2$, —CN, —(CF$_2$)$_n$—CF$_3$ (where n=1-20 inclusive, and preferably 1-8, 3-6, or 4-5), olefins, and the like. In addition to these, those mentioned above as forming part of the example SAM-forming molecules can also be used more generally. In the above list, R is hydrogen or an organic group such as a hydrocarbon or an alkyl. As used herein, the term "hydrocarbon" includes alkyl, alkenyl, alkynyl, cycloalkyl, aryl, alkaryl, aralkyl, and the like. The hydrocarbon group may, for example, comprise methyl, propenyl, ethynyl, cyclohexyl, phenyl, tolyl, and benzyl groups. The term "fluorinated hydrocarbon" is meant to refer to fluorinated derivatives of the above-described hydrocarbon groups. In still another set of embodiments, the molecule may comprise a sulfonate group (—SO$_3^-$).

The molecules described herein may be synthesized using any methods that are available to those of ordinary skill in the art. Some methods of synthesis are described briefly below; more detailed descriptions are described in the Examples section. Synthesis of alkanethiols used for patterning multiple, aligned SAMs is shown in FIG. 2; this figure describes the synthesis of the photocleavable alkanethiols. As a non-limiting example, to generate HS(CH$_2$)$_{11}$(EG)$_2$NPOC, a photocleavable thiol, a trityl-protected form of mercaptoundecanoic acid may be coupled to one amino group in H$_2$N(CH$_2$CH$_2$O)$_2$CH$_2$CH$_2$NH$_2$. The terminal amine of this compound can be allowed to react with MeNPOC; removal of the trityl protecting group generated HS(CH$_2$)$_{11}$(EG)$_2$NPOC. FIG. 1 describes the use of this alkanethiol to pattern multiple, aligned SAMs.

As used herein, "affinity" refers to the degree and strength of attraction between a first entity (e.g., a molecule) and a second entity, which is reflective of the propensity of the first entity to attach to the second entity when the first and second entity are in proximity with each other. Thus, as used herein, a molecule (which may be attached to a substrate) may have an affinity for an entity is able to attach to and, in some cases, bind to the entity. The molecule may be able to attach to the entity by any suitable mechanism, for example, a physical mechanism, such as physical adsorption, charge interactions, hydrophobic effects, van der Waals interactions, electrostatic attraction, magnetic attraction, molecular intercalation, etc., and/or via bond-forming mechanisms, such as chemisorption, covalent bond formation, hydrogen bond formation, and the like. In one embodiment, the molecule is a binding partner. The term "binding partner" refers to a molecule that can undergo binding with a particular molecule. Biological binding partners are examples. For example, Protein A is a binding partner of the biological molecule IgG, and vice versa.

In addition, in certain embodiments, functional groups comprising an affinity tag may be employed. The term "affinity tag" is given its ordinary meaning in the art. An affinity tag is any biological or chemical material that can readily be attached to a target biological or chemical material. Affinity tags may be attached to a target biological or chemical molecule by any suitable method known in the art. For example, in some embodiments, the affinity tag may be attached to a target nucleic acid sequence using a nucleic acid sequence complementary to the target nucleic acid sequence. As another example, an affinity tag such as biotin may be chemically coupled, for instance covalently, to a target protein or peptide, by allowing binding of biotin to an avidin and/or streptavidin moiety fastened with respect to the target protein or peptide.

The term "biological binding" refers to the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of molecules including proteins, nucleic acids, glycoproteins, carbohydrates, hormones and the like. Specific examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc.

In some of the embodiments described herein involving SAMs formed of SAM forming molecules having a functional group, the SAMs may be formed that comprise molecules having a particular functional group, the SAMs may be formed that consist essentially of molecules having a particular functional group, or the SAMs may be formed that consist of molecules having a particular functional group. In certain embodiments, SAMs may be formed comprising a plurality of molecules providing a plurality of different functional groups.

In one set of embodiments, the functional group may be chosen from a wide variety of compounds or fragments thereof which will render the SAM generally or specifically "biophilic" as this term is defined below. "Generally biophilic" functional groups are those that would have a tendency to promote the binding, adherence, or adsorption of biological materials such as, for example, intact cells (e.g., "cytophilic" functional groups), fractionated cells, cellular organelles, proteins, lipids, polysaccharides, simple carbohydrates, complex carbohydrates, nucleic acids, etc. Generally biophilic functional groups can include hydrophobic groups or alkyl groups with charged moieties such as COO$^-$, PO$_3$H$^-$, or 2-imidazolo groups, and/or compounds or fragments of compounds such as extracellular matrix proteins, fibronectin, collagen, laminin, serum albumin, polygalactose, sialic acid, one or more amino acids, e.g. peptide sequences such as RGD or GRGD, antibodies, and various lectin binding sugars. "Specifically biophilic" functional groups are those that selectively or preferentially bind, adhere or adsorb a specific type or types of biological material so as, for example, to identify and/or isolate the specific material from a mixture of materials. Specifically biophilic materials include antibodies or fragments of antibodies and their antigens, cell surface receptors and their ligands, nucleic acid sequences and many others that are known to those of ordinary skill in the art. The choice of an appropriate biophilic functional group depends on considerations of the biological material sought to be bound, the affinity of the binding required, availability, ease of use, effect on the ability of the SAM-forming compound to effectively form a SAM, and cost. Such selection is within the knowledge, ability and discretion of one of ordinary skill in the art.

In another set of embodiments, the functional group may be chosen from a wide variety of compounds or fragments thereof which will render the SAMs "cytophilic," that is, adapted to promote cell attachment. Molecular entities creating cytophilic surfaces are well known to those of ordinary skill in the art and include antigens, antibodies, cell adhesion molecules, extracellular matrix molecules such as laminin, fibronectin, synthetic peptides, carbohydrates, peptide sequences such as RGD, and the like.

In another set of embodiments, the functional group may be chosen from a wide variety of compounds or fragments thereof which will render the SAM "biophobic" as that term is defined below. "Biophobic" SAMs are those with a generally low affinity for binding, adhering, or adsorbing biological materials such as, for example, intact cells, fractionated cells, cellular organelles, proteins, lipids, polysaccharides, simple carbohydrates, complex carbohydrates, and/or nucleic acids. Biophobic functional groups can include polar but uncharged groups including unsaturated hydrocarbons. In certain embodiments, biophobic functional groups can include hydrophilic groups, such as the polyethylene glycol and/or polypropylene glycol moieties previously discussed.

In yet another set of embodiments, the functional groups may be chosen from a wide variety of compounds or fragments thereof which will render the SAM "cytophobic," i.e., such that the SAM has a generally low affinity for binding, adhering, or adsorbing cells. Molecular entities known to create cytophobic surfaces can be selected by those of ordinary skill in the art and include, for example, but not limited to, those groups mentioned above as being biophobic, such as uncharged functional groups such as unsaturated hydrocarbons, or polyethylene glycol groups, etc.

In certain embodiments, the functional groups may be chosen to render the SAM-coated surface hydrophobic and/or hydrophilic. As used herein, the terms "hydrophobic" and "hydrophilic" are given their ordinary meaning as used in the art. In certain cases, a hydrophilic surface may also be cytophobic and/or biophobic, while a hydrophobic surface may also be, in some cases, cytophilic and/or biophilic. The degree of hydrophilicity of a hydrophilic and/or a hydrophobic surface can be readily determined and controlled via proper selection of SAMs bearing particular expressed functional groups as determined through no more than routine experimentation by those of ordinary skill in the art, for example, by using contact angle measurements, determining the water/oil partition coefficient of the molecules and/or the functional groups that comprise the SAM, etc. In some cases, the terms "hydrophobic" and "hydrophilic" are defined relative to each other, where the hydrophilic entity has a greater affinity to water than does the hydrophobic entity.

Thus, in one set of embodiments, a photocleavable alkanethiol may be used that contains one or more functional groups. One non-limiting example is a photocleavable alkanethiol, $HS(CH_2)_{11}EG_6NPOP(GRGD)$, containing a photocleavable linker that allows functional groups to be added beyond the photocleavable group, NPOP, for example, a peptide sequence such as Gly-Arg-Gly-Asp (GRGD) (e.g., which may be synthesized on a Wang resin). In this particular example, the photocleavable linker can be coupled to this peptide, and then a trityl-protected alkanethiol can be coupled to the photocleavable linker on the solid support. The removal of all protecting groups (except the photocleavable linker) produced-$HS(CH_2)_{11}EG_6NPOP(GRGD)$. FIG. 1 also shows the use of this alkanethiol to pattern multiple, aligned SAMs.

As is apparent from the description, the use of self-assembled monolayers that expose a variety of chemical functionalities on surfaces according to the invention is a common feature of many embodiments of the invention. In addition to the extensive and enabling description of various functional groups useful or potentially useful as exposed functionalities on SAMs utilized for particular purposes, additional disclosure related to hydrophobic, hydrophilic, biophobic, biophilic, cytophobic, cytophilic, and other functionalities incorporated into SAMs and/or SAM-forming molecules can be found in the following references, all incorporated herein by reference: U.S. Provisional Patent Application Ser. No. 60/443,446, filed Jan. 29, 2003, entitled "Alteration of Surface Affinities," by Jiang, et al.; U.S. Pat. No. 6,472,148, entitled "Molecular Recognition at Surfaces Derivatized with Self-Assembled Monolayers," by Bamdad, et al.; U.S. Pat. No. 6,368,838, entitled "Adhering Cells to Cytophilic Islands Separated by Cytophobic Regions to Form Patterns and Manipulate Cells," by Singhvi et al.; U.S. Pat. No. 6,355,198, entitled "Method of Forming Articles Including Waveguides via Capillary Micromolding and Microtransfer Molding," by Kim et al.; U.S. Pat. No. 6,180,239, entitled "Microcontact Printing on Surfaces and Derivative Articles," by Whitesides, et al.; U.S. Pat. No. 5,976,826, entitled "Device Containing Cytophilic Islands that Adhere Cells Separated by Cytophobic Regions," by Singhvi, et al.; U.S. Pat. No. 5,900,160, entitled "Methods of Etching Articles via Microcontact Printing," by Whitesides, et al.; U.S. Pat. No. 5,776,748, entitled "Methods of Formation of Microstamped Patterns on Plate for Adhesion of Cells and Other Biological Materials, Devices and Uses Therefor," by Singhvi, et al.; U.S. Pat. No. 5,512,131, entitled "Formation of Microstamped Patterns on Surfaces and Derivative Articles," by Kumar, et al.; U.S. Pat. No. 5,079,600, entitled "High Resolution Patterning on Solid Substrates," by Schnur, et al.; U.S. patent application Ser. No. 09/808,745, entitled "Cell Patterning Technique," by Ostuni, et al.; International Pat. Apl. Pub. No. WO 02/06407, entitled "Surfaces that Resist the Adsorption of Biological Species," by Whitesides, et al.; International Pat. Apl. Pub. No. WO 01/89788, entitled "Patterning of Surfaces Utilizing Microphilitic Stamps including Three-Dimensionally Arrayed Channel Networks," by Whitesides, et al.; Kleinfeld, et al., "Controlled outgrowth of dissociated neurons on patterned substrates," *Journal of Neuroscience*, 8(11):4098, 1988; Westermark, B., "Growth Control in Miniclones of Human Glial Cells", *Experimental Cell Research*, 111:295-299, 1978; Britland, S., et al., "Micropatterned Substratum Adhesiveness: a Model for Morphogenetic Cues Controlling Cell Behavior," *Experimental Cell Research*, 198:124-129, 1992; Singhvi, R., et al., "Engineering Cell Shape and Function," *Science*, 264:696, 1994; Lopez, G. P., et al., "Convenient Methods of Patterning the Adhesion of Mammalian Cells to Surfaces Using Self-Assembled Monolayers of Alkanethiolates on Gold," *Journal of the American Chemical Society*, 115:5877-5878, 1993; U.S. Provisional Patent Application Ser. No. 60/443,466, filed Jan. 29, 2003, entitled "Alteration of Surface Affinities," by Jiang, et al.; and International Patent Application No. PCT/US2004/002498, filed Jan. 29, 2004, entitled "Alteration of Surface Affinities," by Jiang, et al.

An enormous variety of patterns may be produced and a multiplicity of SAMs may be employed to create patterns of one or more types of cells. As discussed previously, the SAMs employed for embodiments involving cell binding and manipulation may be either generally or specifically biophilic/cytophilic or biophobic/cytophobic as applied (or certain surfaces may contain certain regions with generally biophilic/cytophilic or biophobic/cytophobic SAMs, while other regions contain specifically biophilic/cytophilic or biophobic/cytophobic SAMs). In some cases, the SAMs may be modified after SAM formation to become generally or specifically biophilic/cytophilic or biophobic/cytophobic by chemical modification of exposed functional groups. For example, when several SAMs are present in a pattern but only one is cytophilic, a first type of cell may be adhered to the cytophilic SAM and then a cytophobic SAM may be chemically modified in situ so as to become cytophilic. In some cases, a second cell type may then be adhered to the newly cytophilic SAM and this process can be repeated to create a complex pattern of different cell types. Similarly, if several SAMs are present in a pattern but only one is biophilic, a first type of biological entity may be adhered to the biophilic SAM and then a biophobic SAM may be chemically modified in situ so as to become biophilic. A second biological entity, may then be adhered to the newly biophilic SAM in some cases, and this process can be repeated to create a complex pattern.

In another aspect of the present invention, SAM-patterned substrates are provided which may be used to bind or adsorb proteins and/or other biological entities (e.g., cells) in specific and predetermined patterns. As is known to those of ordinary skill in the art, phenomena associated with the adsorption of proteins to solid synthetic materials are important in many areas of biotechnology including, for example, production, storage and delivery of pharmaceutical proteins, purification of proteins by chromatography, design of biosensors and prosthetic devices, and production of supports for attached tissue culture (see, for example, *ACS Symposium Series* 343, T. A. Horbett and J. L. Brash, Eds., Am. Chem. Soc., Washington, D.C., 1987; J. D. Andrade, Surface and Interfacial Aspects of Biomedical Polymers: Protein Adsorption, Plenum Press, N.Y., 1985; *Materials Research Society Proceedings* 252, L. G. Cima and E. Ron, Eds., *Mat. Res. Soc., Pittsburgh, Pa.,* 1992). A number of researchers have demonstrated the formation of patterns of proteins (see, for example, A. S. Lea, et al., *Langmuir* 8:68-73, 1992). These have often relied on photolithography to create the patterns (see, for example, S. K. Bhatia, et al., *J. Am. Chem. Soc.,* 114:4432-4433, 1992; S. K. Bhatia, et al., *Anal. Biochem.,* 208:197-205, 1993). The present invention provides for relatively inexpensive and efficient patterning of proteins and manipulation of the affinity of a substrate for proteins via utilization of a non-chemical force-creating field and/or forces such as an electric field, with features of the pattern as small as 0.1-1 microns in some cases.

In similar embodiments, a substrate can be created with patterned SAMs thereon as described previously. Depending upon the desired application, the pattern may include islands or parallel rows of SAMs with different properties. One portion of the substrate may be biophilic/cytophilic and the other may be biophobic/cytophobic as applied, or they may be modified so as to become biophilic/cytophilic or biophobic/cytophobic subsequent to SAM formation, i.e., through exposure to an electric field as described. In a particular embodiment, a substrate surface may include a biophilic region of SAMs and a biophobic region of SAMs and, subsequent to binding a protein or proteins to the biophilic SAM, the biophobic region may be modified so as to become biophilic, i.e., through biophilic SAM removal via exposure to an electric field. In this way, a pattern of two or more protein groups may be created. Similarly, patterns of more than two SAMs may be used to create more complicated patterns of proteins in accordance with the present invention. The extent of binding of the proteins to the substrate may also be controlled and/or changed by the use of an electric field (or other non-chemical force-creating field). For example, proteins attached to SAMs present in certain portions of the substrate may be selectively detached by application of an electric field to those portions, in some cases without creating an electric field capable of SAM detachment in other portions of the substrate. In many embodiments, the electric field may be applied to the substrate to detach SAM-forming molecules as provided according to the invention even in the presence of animal serum (e.g., calf serum or human serum), or in the presence of other, undefined media (i.e., media in which the exact chemical composition is not known), whereas typical prior art techniques for electric field-mediated alteration of SAMs on surfaces do not have this capacity (see, e.g., Yousaf, et al., *Angew. Chem. Int. Ed.,* 40:1093, 2001).

In certain embodiments, a substrate with patterned proteins may be prepared as described above and cells may then be allowed to adhere to the patterned proteins to form a substrate having patterned cells thereon. In some embodiments, the proteins may include extracellular matrix proteins or ligands for receptors such as collagen, fibronectin or laminin; or specific cell receptors such as integrins. In certain embodiments, the patterned protein can mediate the cell adhesion behavior of the patterned cells. In yet another embodiment, a patterned substrate of biophilic and biophobic SAMs may be created and a wide variety of non-protein compounds may first be adhered to the pattern to mediate cell binding. Such compounds include but are not limited to sialic acid, lectins, polygalactose and other carbohydrates.

The surface material of the substrate may comprise the entire substrate onto which the patterned SAMs of the present invention are bonded or otherwise attached, or may be a thin film deposited upon an article. Where a separate substrate is used, it may comprise any of a wide variety of biological, non-biological, organic, or inorganic materials, or a combination of any of these existing as particles, strands, precipitates, gels, sheets, tubing, spheres, containers, capillaries, pads, slices, films, slides, plates, etc. In certain embodiments, the substrate of the present invention is substantially planar, although it need not be according to other embodiments. The substrate may be formed of a conductive material, a semiconducting material, and/or non-conducting material, and may comprise, for example, alumina, plastic or other organic polymers including acrylonitrile-butadine-styrene copolymers, polysulfone, metals and/or any of the above materials described with respect to the surface material of the present invention. The substrate may additionally include a bonding layer, for example a thin titanium film, to promote adhesion between the surface material and the substrate.

The surface material, for embodiments involving coated substrates, is generally of a thickness on the order of 500 microns, but may be substantially thicker or may be substantially thinner. For example, when a substrate as a base material is employed, the surface material may have a thickness of less than about 100 nanometers, less than about nanometers, or even less than about 6 nanometers. When a thin film of surface material is employed, and a transparent substrate supports the surface material, a transparent base support for a SAM can result, and this may be advantageous in standard light or electron microscopic or spectrophotometric detection or analysis of any biological material interacting with a SAM on the surface material.

In certain sets of embodiments, SAMs formed on a substrate surface may be modified after formation for a variety of purposes. For example, a SAM-forming compound on a substrate may have a functionality including a protecting group which may be removed to effect further modification of the SAM (i.e., to produce a specific surface chemistry). For instance, a photoremovable protecting group may be used, where the group is advantageously selected such that it may be removed without disturbance of the SAM of which it is a part. For example, a protective group may be selected from a wide variety of positive light-reactive groups, for example, nitroaromatic compounds such as o-nitrobenzyl derivatives or benzylsulfonyl. A variety of photoprotecting groups can be used to protect different functional groups, e.g., alcohols, carboxylic acids, thiols, etc. Photoremovable protective groups can be readily selected by those of ordinary skill in the art and are described in, for example, U.S. Pat. No. 5,143,854, issued Sep. 1, 1992; Patchornik, *J. Am. Chem. Soc.*, 92:6333, 1970; or Amit, et al., *J. Org Chem.*, 39:192, 1974, all of which are incorporated herein by reference. Alternatively, a reactive group may be provided on an exposed portion of a SAM that may be activated or deactivated by electron beam lithography, x-ray lithography, or any other suitable type of radiation exposure. Such protections and deprotections of functional groups may aid in chemical or physical modification of an existing surface-bound SAM, for example in lengthening existing molecular species forming the SAM, for example, as described in U.S. Pat. No. 5,143,857, incorporated herein by reference.

As a specific example, when only a subset of cells in a sample are desired to be immobilized to an article of the invention, for example, the white blood cells in a blood sample containing both red and white blood cells, a specifically biophilic SAM may be chosen that will selectively bind the cells of interest and, subsequent to binding, the extraneous cells may be washed away. Given a particular set or subset of cells to be studied, the choice of a biophilic SAM specific to those cells is within the ability of one of ordinary skill in the art and, given the disclosures herein, one of ordinary skill in the art is enabled to produce appropriate patterned biophilic SAMs specific for those cells.

Many methods may be used to apply and attach the SAM-forming molecules to a substrate surface. For example, the SAM-forming molecules may be applied to the substrate by stamping or micropatterning techniques, organic synthesis techniques, and the like. A variety of suitable methods to attach the SAM to the substrate are known in the art and may be chosen by one of ordinary skill in the art to suit a particular purpose.

For example, in one set of embodiments, the SAM-forming molecules may be patterned on the substrate using a stamp in a "printing" process in which the "ink" consists of a solution including a SAM-forming compound capable of attaching to a surface to form a SAM. The ink is applied to the surface of a substrate using the stamp and deposits a SAM on the substrate in a pattern determined by the pattern on the stamp. The substrate may be stamped repeatedly with the same or different stamps in various orientations and with the same or different SAM-forming solutions. In addition, after stamping, portions of the substrate which remain uncovered by SAMs may optionally be derivatized using any suitable technique known in the art, for example, exposure of the uncovered portions to another solution containing a SAM-forming compound. The SAM-forming or derivatizing solutions can be chosen such that the regions of the finished substrate defined by the patterns differ from each other in their ability to bind to materials such as biological or biochemical materials (e.g., proteins, drugs, cells, etc.). As one example, cytophobic SAM-forming compounds may be patterned on a cytophilic substrate to create a pattern of cytophobic SAMs and cytophilic regions not containing SAMs (or, alternatively, containing cytophilic SAMs), such that certain cells applied to the substrate can bind to the cytophilic regions, but are unable to bind to regions containing the SAMs; thereafter, application of a suitable electric field to the substrate, or to portions of the substrate, may detach the SAMs from the substrate or those in those portions subjected to the field, permitting the cells to then migrate into those portions where the SAMs have been detached.

In certain embodiments, the stamp described above may be formed via a molding process. The mold used to form the stamp may be a commercially available item such as a transmission electron microscopy grid or any other corrugated material possessing a pattern which is desired to be reproduced on the stamp, or a mold especially prepared by any of a variety of methods known in the art. The stamp may be produced by casting a material, e.g., a polymer such as a silicon polymer (e.g., polydimethylsiloxane) onto a mold having the desired pattern. Various techniques for forming stamps for patterning SAMs are known in the art and several are described in detail in, for example, U.S. Pat. No. 6,368,838, by Singhvi, et al., entitled "Adhering Cells to Cytophilic Islands Separated by Cytophobic Regions to form Patterns and Manipulate Cells," hereby incorporated by reference, to which the reader is referred to for more details.

As mentioned above, in some embodiments, after a desired SAM pattern has been formed on the substrate by stamping, the portion of the substrate which is bare or not covered by the stamped SAM may be further reacted or otherwise processed, for example, to add chemical functionality thereto, or to add one or more additional regions containing SAMs. For example, the portion of the substrate which is not covered by the stamped SAM may, in some cases, be derivatized by exposing it to a second or "filling" solution with characteristics differing from the first solution which was used as the ink for forming the initial stamped pattern. This exposure may be accomplished using stamping techniques similar to those previously described, by dipping the substrate in a bath of solution, by pouring the solution onto the substrate, or by any other convenient method which preferably does not disrupt the patterned SAM. The second solution in certain embodiments may form a SAM over the surface of the plate which is not already covered by the patterned SAM of the ink. That is, the second of filling solution may contain a second SAM-forming compound which will form a second or "filling" SAM on the bare portions of the substrate. The result of such an embodiment can be a plate essentially completely covered by complementary patterns of two or more SAMs of differing properties. As an example, two SAM-forming compounds able bind different cell types may be patterned on a substrate such that one SAM region is able to bind a first cell type and a second SAM region separate from the first region is able to bind a second cell type; application of an electric field to the substrate may then cause selective detachment of one of the SAMs, and consequently, selective detachment of only one of the cell types.

Of course, it is not necessary in all embodiments to derivatize or otherwise react or coat any bare portions of the surface remaining after forming patterned SAMs. Depending upon the surface used, the bare surface may have the desired biophilic or biophobic characteristics and, thus, any additional steps may be omitted. For example, when it is desired that cells adhere to a portion of a surface, exposure of the bare surface to a medium containing serum may be sufficient to facilitate binding of the cells.

In certain embodiments, the substrate may be patterned such that one or more regions on the surface are able to bind cells and/or other entities, while a second region on the surface is unable to bind the cells and/or other entities; exposure of the second region to an electric field may then change the affinity of the second region (e.g., by detaching SAM-forming molecules at their point of attachment to the surface) so as to allow the second region to then bind the cells and/or the other entities. The regions may be distributed in any suitable pattern on the surface, for example, half of the substrate may be cytophilic and/or biophilic, while the other half of the substrate may be cytophobic and/or biophobic. In another embodiment, the two or more regions may be distributed such that one or more regions forms channels or isolated islands within another region. As used herein, an "island" is a contiguous region adapted to bind to a particular entity or class of similar entities, such as cells and/or other entities generally, or a particular type of cell or type of entities.

Multiple, aligned patterns of SAMs may be used to pattern multiple types of cells and for studying cell-cell signaling (e.g., where one cell type is separated from the other).

In one set of embodiments, a method of using certain articles and substrates of the invention for assaying the effects of various treatments and compounds such as drugs on cells is provided. In one embodiment, the invention provides the capability to assay the effects of various treatments or compounds on various cells adhered to a substrate. As one example, once a suspension of cells has been applied to a substrate containing cytophilic regions and SAM-coated cytophobic regions, a period of time is allowed to elapse in order to allow the cells to bind to the cytophilic regions of the substrate. Excess fluid including unbound cells may then be washed away. The cells may then be subjected to a treatment or exposed to a compound in situ or, in some situations, the cells may be pre-treated before being introduced to the substrate for attachment. The effects of the treatment or compound on the cells may then be individually assayed in a manner appropriate to the cell type and the treatment or compound being studied, for example, using analytical techniques such as those previously described. For example, cells may be removed from a surface by exposing at least a portion of the surface to light, thereby cleaving at least a portion of the molecules forming a SAM.

In one set of embodiments, a cell motility assay of the invention can be automated. For example, in one embodiment, exposure of the substrate to the electric field, and/or detection of cell positions and/or migration behavior on the substrate may be automated, for example, with a computer or a mechanical system.

In some cases, a detector unit able to detect cell positions and/or cell migration behavior may include a multiplicity of individual detectors in an array corresponding and addressable to individual positions, regions, and/or islands on the substrate, as described above. For example, the detector may be a CCD camera or a semiconductor chip. In certain cases, the effect of a treatment or compound on many cells and/or cell types may be assessed simultaneously, with minimal user involvement.

In certain cases, the above-described embodiments, which allow for plating of cells at high densities, can be employed for high throughput tests of potentially useful treatments including pharmacological or toxicological compounds. In particular, the present invention provides assays which allow qualitative and quantitative changes in cell behavior or position in response to a change in the area over which they are permitted to adhere, to be determined and/or measured as a function of exposure to a given treatment or compound. In other embodiments, the inventive techniques can be utilized to assay various aspects related to the proliferation, differentiation, orientation, spreading, motility and/or migration of cells.

The following examples are intended to illustrate certain embodiments of the present invention, but do not exemplify the full scope of the invention.

Example 1

Syntheses of Alkanethiols Used for Patterning Multiple, Aligned SAMs

This example describes procedures for synthesizing certain photocleavable alkanethiols that were used in the formation of SAMs on a gold surface. As would be understood by those of ordinary skill in the art, similar techniques as described below and/or other procedures for synthesizing known in the art could be employed to make various other photocleavable alkanethiols within the scope of the invention. Similarly, modifications of the techniques below and/or use of a variety of other know techniques could be employed by those of ordinary skill in the art to synthesize other molecules, such as SAM-forming molecules, having a moiety able to react with and bind to a surface of an article of the invention (e.g. in certain embodiments a silane moiety or thiol moiety), and a photocleavable moiety(s).

FIG. 2 describes the synthesis of photocleavable alkanethiols. Briefly, a trityl-protected form of mercaptoundecanoic acid was coupled to one amino group in $H_2N(CH_2CH_2O)_2CH_2CH_2NH_2$. The terminal amine of this compound was allowed to react with MeNPOC; removal of the trityl protecting group generated $HS(CH_2)_{11}(EG)_2NPOC$ (5). FIG. 1 describes the use of this alkanethiol to pattern multiple, aligned SAMs.

A second embodiment of a photocleavable alkanethiol, $HS(CH_2)_{11}EG_6NPOP(GRGD)$, contained a photocleavable linker that allowed functional groups to be added beyond the photocleavable group, NPOP. We synthesized the peptide sequence Gly-Arg-Gly-Asp (GRGD) on a Wang resin, (Fields, G. B.; Noble, R. L. Int. J. Pept. Protein Res. 1990, 35, 161-214) coupled the photocleavable linker to this peptide, and then coupled a trityl-protected alkanethiol to the photocleavable linker on the solid support. The removal of all protecting groups (except the photocleavable linker) produced $HS(CH_2)_{11}EG_6NPOP(GRGD)$ (8). FIG. 1 also shows the use of this alkanethiol to pattern multiple, aligned SAMs.

Materials. All chemicals were purchased from Aldrich (St. Louis, Mo.) unless stated otherwise. MeNPOC was obtained from Cambridge Major Laboratories (Germantown, Wis.). Anti-dinitrophenol delipidized rabbit anti-serum (anti-DNP rIgG), monoclonal anti-biotin mouse immunoglobulin G (anti-biotin mIgG), monoclonal anti-bovine serum albumin mouse IgG (anti-BSA mIgG), anti-bovine serum albumin rabbit IgG (anti-BSA rIgG), phosphate-buffered saline (PBS), and fibrinogen were purchased from Sigma (St. Louis, Mo.). Texas Red labeled anti-rabbit donkey IgG (TR-anti-rabbit IgG) was obtained from Amersham Biosciences (Newark, N.J.). Alexa Fluor 488 labeled anti-mouse IgG (AF488-anti-mouse IgG) was obtained from Molecular Probes (Eugene, Oreg.). The quantities of antibodies used are quoted as a ratio relative to the stock concentration acquired commercially, for example, 1:10 implies a 1:10 dilution in blocking buffer (0.05% Tween (w/v) in PBS) of the concentration provided by the supplier was used. H-1000 mounting medium for fluorescence was obtained from Vector Laboratories (Burlingame, Calif.).

Analytical HPLC was run on a Varian instrument (Walnut Creek, Calif.) with a Microsorb C18 column (5 µm, 4.6×250 mm) using a linear gradient of water with 0.1% trifluoroacetic acid (TFA) (A) followed by acetonitrile containing 0.08%

TFA (B), at a flow rate of 1.2 mL/min (UV detection at 214 nm). Preparative reverse-phase HPLC was performed using a Varian apparatus on a C18 column (5 μm, 10×250 mm) at a flow rate of 6 mL/min (UV detection at 214 nm). Amino acids and derivatives were obtained from Novabiochem (San Diego, Calif.). 4-{4-[1-(Fmoc-amino)ethyl]-2-methoxy-5-nitrophenoxy}butyric acid was purchased from Advanced Chemtech (Louisville, Ky.). Mass spectra of organic molecules (not SAMs) were obtained by MALDI-TOF mass spectrometry on a Voyager-DE PRO (PerSeptive Biosystems, Foster City, Calif.). MALDI-TOF mass spectra of SAMs were analyzed on a Voyager-DE Biospectroscopy mass spectrometer using 2,4,6-trihydroxyacetophenone (5 μL of a 10 mg/mL solution in acetone) as a matrix. SPR experiments were performed using a Biacore 1000 SPR instrument (Piscataway, N.J.). Solutions of fibrinogen (1 mg/mL, PBS buffer) were used in all SPR experiments, and solutions were filtered through 0.2-μm poly(vinylidene fluoride) filters immediately before use. Fluorescence images were recorded using an ORCA-ER Hamamatsu charge coupled device camera mounted on a DMIRB Leica inverted fluorescence microscope (DSC Optical Services; Newton, Mass.). An AB-M Mask Aligner (AB-M Inc.; San Jose, Calif.) was used as a light source for 220 and 365 nm wavelengths. Mirrors that select for each of these wavelengths were used separately during the experiments.

Figure 2A:
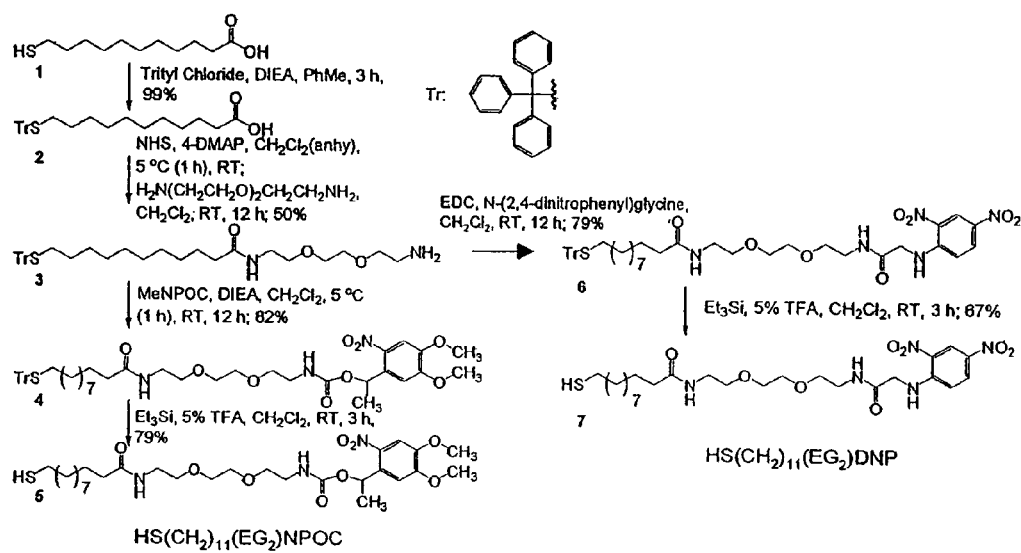
FIG. 2 is a schematic illustration showing synthetic strategies for (A) $HS(CH_2)_{11}(EG_2)NPOC$ and $HS(CH_2)_{11}(EG_2)DNP$ and for (B) $HS(CH_2)_{11}EG_6NPOP(GRGD)$ (on a solid-phase support).

The alkanethiols (2-{2-[2-(11-mercapto-undecanoylamino)-ethoxy]-ethoxy}-ethyl)-carbamic acid 1-(4,5-dimethoxy-2-nitro-phenyl)-ethyl ester ($HS(CH_2)_{11}(EG)_2$NPOC) and 11-mercapto-undecanoic acid [2-(2-{2-[2-(2,4-dinitro-pheylamino)-acetylamino]-ethoxy}-ethoxy)-ethyl]-amide ($HS(CH_2)_{11}(EG)_2$DNP) were prepared according to the reaction scheme shown in FIG. 2A. All reactions involving MeNPOC and NPOP were carried out in aluminum-foil-coated flasks to exclude light during reactions.

Synthesis of 11-Tritylsulfanyl-undecanoic Acid (2). To a solution of trityl chloride (4.6 g, 17 mmol) and diisopropyl-ethylamine (DIEA, 4.2 g, 33 mmol) in toluene (50 mL) was added 11-mercaptoundecanoic acid, 1 (6.0 g, 14 mmol), and the solution was stirred at room temperature for 3 h. The solution was evaporated, and the product separated between dichloromethane and water. The organic phase was washed with water (2×100 mL), dried ($MgSO_4$), filtered, and concentrated to yield crude 2 (6.3 g, 13.6 mmol, 97%). $^1$H NMR ($CDCl_3$, 500 MHz): δ1.14-1.42 (br m, 14H), 1.59-1.68 (br t, 2H), 2.06-2.09 (br m, 2H), 2.36-2.40 (t, 2H), 7.19-7.23 (m, 6H), 7.26-7.29 (m, 9H).

11-Tritylsulfanyl-undecanoic Acid {2-[2-(2-Aminoethoxy)ethyl]-ethyl}-amide (3). To a solution of N-hydroxysuccinimide (0.26 g, 2.3 mmol) and a catalytic amount of 4-(dimethylamino)pyridine in anhydrous dichloromethane (50 mL) was added crude 2 (1.03 g, 2.2 mmol). Dicyclohexylcarbodiimide (0.46 g, 2.2 mmol) was added to the solution. The reaction was cooled for the first hour at 5° C. and left to react at room temperature overnight. The solution was diluted with dichloromethane, filtered to remove dicyclohexylurea, and evaporated to dryness to yield the active ester of 2 (1.1 g, 2 mmol). To a stirred solution of this active ester (1.1 g, 2 mmol) in dichloromethane (50 mL) was added 2,2'-(ethylenedioxy)bisdiethylamine (5.1 g, 34 mmol) over a period of 30 min. The reaction was left at room temperature for 12 h. The solution was filtered, washed with water (3×200 mL), dried ($MgSO_4$), and concentrated to yield 3 (1.25 g, 2.1 mmol, 95%). $^1$H NMR ($CDCl_3$, 500 MHz): δ1.24-1.42 (br m, 14H), 1.59-1.68 (br t, 2H), 2.06-2.09 (m, 2H), 2.78-2.85 (br t, 2H), 3.38-3.42 (m, 4H), 3.46-3.51 (m, 4H), 3.58-3.63 (s, 4H), 7.19-7.23 (m, 6H), 7.26-7.29 (m, 9H). $C_{36}H_{50}N_2O_3S$ (590.35): m/z 591.1 [M+H$^+$]+.

(2-{2-[2-(11-Tritylsulfanyl-undecanoylamino)-ethoxy]-ethoxy}-ethyl)-carbamic Acid 1-(4,5-Dimethoxy-2-nitro-phenyl)-ethyl Ester (4). To a stirred solution of 3 (1.03 g, 1.74 mmol) and DIEA (0.26 g, 2.0 mmol) in dichloromethane (50 mL) was added MeNPOC (0.59 g, 2.0 mmol) over a period of 30 min. The reaction was cooled for the first hour at 5° C. and then left to react at room temperature overnight. The solution was washed with 0.01 M HCl (1×100 mL), 0.2 M NaOH (1×100 mL), and saturated aqueous NaCl solution (1×100 mL). The solution was dried ($MgSO_4$) and evaporated to dryness. The crude compound was chromatographed ($SiO_2$/EtOAc→MeOH) to yield 1.2 g (1.4 mmol; 82%) of 4 as a yellow oil. $^1$H NMR ($CDCl_3$, 500 MHz): δ1.24-1.42 (br m, 10H), 1.59-1.71 (br m, 4H), 1.82-1.93 (br t, 2H), 2.02-2.11 (br m, 2H), 2.78-2.85 (br t, 2H), 3.38-3.42 (m, 4H), 3.46-3.51 (m, 4H), 3.58-3.63 (s, 4H), 3.63-3.66 (s, 3H), 3.66-3.69 (s, 3H), 6.14 (s, 3H), 6.22-6.31 (br q, 1H), 6.95 (s, 1H), 7.14-7.24 (m, 6H), 7.31-7.39 (m, 9H), 7.45 (s, 1H).

(2-{2-[2-(11-Mercapto-undecanoylamino)-ethoxy]-ethoxy}-ethyl)-carbamic Acid 1-(4,5-Dimethoxy-2-nitro-phenyl)-ethyl Ester, $HS(CH_2)_{11}(EG)_2$NPOC (5).

A solution of trifluoroacetic acid in dichloromethane (5% v/v), 4 (1.2 g, 1.4 mmol), and triethylsilane (0.83 g, 7.1 mmol) was stirred for 3 h at room temperature. The solution was washed with 0.2 M NaOH (2×100 mL) and brine (2×100 mL), dried ($MgSO_4$), and evaporated to dryness. The crude compound was chromatographed ($SiO_2$/EtOAc→MeOH) to yield 0.46 g (0.77 mmol, 54%) of $HS(CH_2)_{11}(EG)_2$NPOC as a thick yellow oil.

$HS(CH_2)_{11}(EG)_2$NPOC, 5: $^1$H NMR ($CDCl_3$, 500 MHz): δ1.24-1.42 (br s, 14H), 1.57-1.68 (br t, 2H), 2.17-2.21 (br m, 2H), 2.51-2.57 (q, 2H), 3.32-3.41 (m, 4H), 3.46-3.51 (m, 4H), 3.58-3.63 (m, 4H), 3.63-3.66 (s, 3H), 3.66-3.69 (s, 3H), 6.14 (s, 3H), 6.22-6.31 (br q, 1H), 6.95 (s, 1H), 7.45 (s, 1H). $C_{28}H_{47}N_3O_9S$ (585.75): m/z 608.9 [M+Na$^+$]+.

11-Tritylsulfanyl-undecanoic Acid [2-(2-{2-[2-(2,4-Dinitro-phenylamino)-acetylamino]-ethoxy}-ethoxy)-ethyl]-amide (6). To a stirred solution of 3 (0.25 g, 0.42 mmol) and N-(3-dimethylaminopropyl)-N'-ethylcarbodiimide hydrochloride (0.1 g, 0.5 mmol) in dichloromethane (50 mL) was added N-(2,4-dinitrophenyl)glycine (0.11 g, 0.51 mmol), and the solution was left to react at room temperature overnight. The solution was washed with 0.01 M HCl (1×100 mL), 0.2 M NaOH (1×100 mL), and brine solution (1×100 mL). The solution was dried ($MgSO_4$) and evaporated to dryness. The crude compound was chromatographed ($SiO_2$/EtOAc→MeOH) to yield 0.26 g (0.33 mmol, 79%) of 6 as a yellow oil. $^1$H NMR ($CDCl_3$, 500 MHz): δ1.12-1.42 (br m, 14H), 1.57-1.62 (br m, 2H), 1.63-1.72 (br t, 2H), 2.12-2.21 (br m, 2H), 3.41-3.61 (br m, 12H), 4.17-4.21 (d, 2H), 5.87-5.92 (br s, 1H), 6.89-6.94 (d, 1H), 7.14-7.24 (m, 6H), 7.31-7.39 (m, 9H), 8.26-8.32 (d, 1H), 9.14-9.21 (br d, 1H). $C_{44}H_{55}N_5O_8S$ (813.38): m/z 812.7 [M−H$^+$]−.

11-Mercapto-undecanoic Acid [2-(2-{2-[2-(2,4-Dinitrophenylamino)-acetylamino]-ethoxy}-ethoxy)-ethyl]-amide, $HS(CH_2)_{11}(EG)_2$DNP (7). A solution of trifluoroacetic acid in dichloromethane (5% v/v), 6 (0.26 g, 0.33 mmol), and triethylsilane (0.19 g, 1.7 mmol) was stirred for 3 h at room temperature. The solution was washed with 0.2 M NaOH (2×100 mL) and brine (2×100 mL), dried ($MgSO_4$), and concentrated. The crude compound was chromatographed ($SiO_2$/EtOAc→MeOH) to yield 0.12 g (0.22 mmol, 67%) of $HS(CH_2)_{11}(EG)_3$DNP as an orange solid.

$HS(CH_2)_{11}(EG)_2$DNP, 7: $^1$H NMR ($CDCl_3$, 500 MHz): δ1.22-1.39 (br s, 14H), 1.58-1.65 (br t, 2H), 2.18-2.21 (br m,

2H), 2.52-2.56 (q, 2H), 3.41-3.49 (m, 4H), 3.52-3.56 (m, 4H), 3.58-3.61 (m, 4H), 4.17-4.21 (d, 2H), 6.89-6.94 (d, 1H), 8.26-8.32 (d, 1H), 9.14-9.21 (br d, 1H). $C_{25}H_{40}N_4O_8S$ (571.69): m/z 594.8 [M+Na$^+$]+.

Figure 2B:
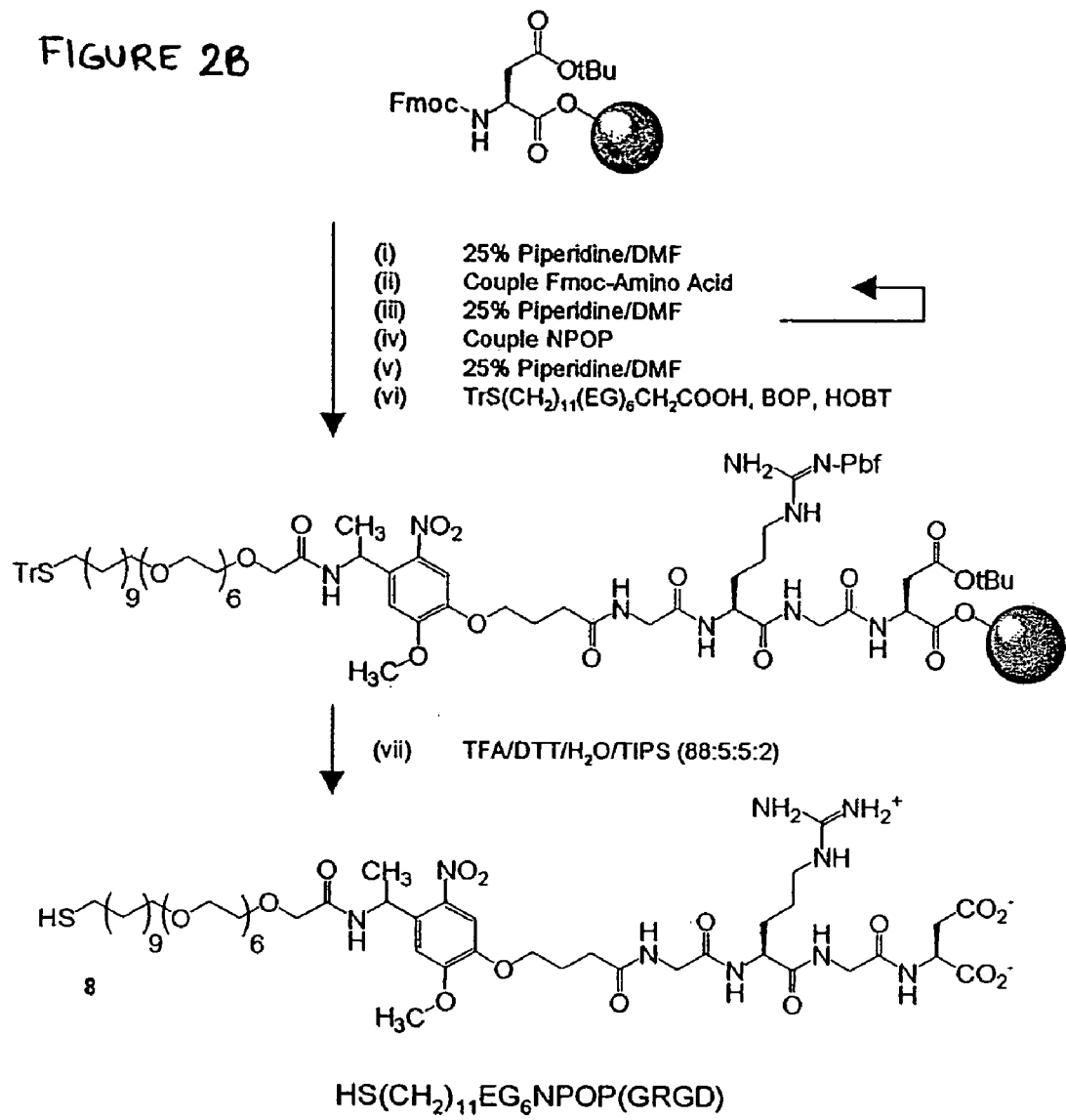

Solid-Phase Synthesis of HS(CH$_2$)$_{11}$EG$_6$NPOP(GRGD) (8). The alkanethiol peptide HS(CH$_2$)$_{11}$EG$_6$NPOP(GRGD), 8, was synthesized using Fmoc-tBu chemistry and stepwise solid-phase methodology (FIG. 2B). Synthesis of protected peptide chains was carried out on a 100-μmol scale starting from Fmoc-Asp(OtBu)-Wang resin. The Fmoc group was removed using 20% piperidine in dimethylformamide (DMF, 1×5 min, 1×15 min) under nitrogen. The resin was filtered and washed with DMF (6×3 min). For each coupling step, a solution of the Fmoc-amino acid (5 equiv), (benzotriazol-1-yloxy)tris(dimethylamino)phosphonium hexafluorophosphate (BOP, 5 equiv), and 1-hydroxybenzotriazole (HOBT, 5 equiv) in DMF and DIEA were added successively to the resin, and the suspension was stirred for 10 min at room temperature. The coupling reaction was monitored using 2,4, 6-trinitrobenzene sulfonic acid (TNBS). After the removal of the last Fmoc protecting group, the resin was washed with DMF and TrS(CH$_2$)$_{11}$(EG)$_6$CH$_2$CO$_2$H (Prochimia, Poland; 2.5 equiv) was coupled using BOP (2.5 equiv), HOBt (2.5 equiv), and DIEA (2.5 equiv) in DMF for 5 h at room temperature. The resin was washed with dichloromethane and diethyl ether and dried under nitrogen. Deprotection of the side chain and cleavage of the peptide from the resin were performed by treatment with TFA, dithiothreitol (DTT), water, and TIPS (triisopropyl-silane) in the ratio 88:5:5:2 (TFA/DTT/H$_2$O/TIPS). After precipitation in cold ether and centrifugation, the deprotected peptide was solubilized and lyophilized. The crude peptide derivative was purified by HPLC (linear gradient, 0-80% B, 40 min) and lyophilized to yield HS(CH$_2$)$_{11}$EG$_6$NPOP(GRGD) (8) as a white powder. HPLC $t_R$ 18.84 min (linear gradient, 0-100% B, 20 min); MS-(MALDI-TOF) m/z 1192.96 [M+1]+.

Example 2

Fabrication of the Photomask Used for Patterning Multiple, Aligned SAMs

This example describes the fabrication of a photomask that is selective to multiple wavelengths, having patterns of squares and triangles (see FIG. 3). This photomask was used as both an area- and wavelength-selective filter. The squares (made in quartz) allowed all wavelengths of light to pass through; the triangles (made in indium tin oxide, ITO) allowed 365 nm light to pass through (but is essentially opaque to light at 220 nm), and the rest of the photomask was covered with chromium, which was opaque to all wavelengths of light used. The photomask, once fabricated, could be used repeatedly.

Figure 3B:
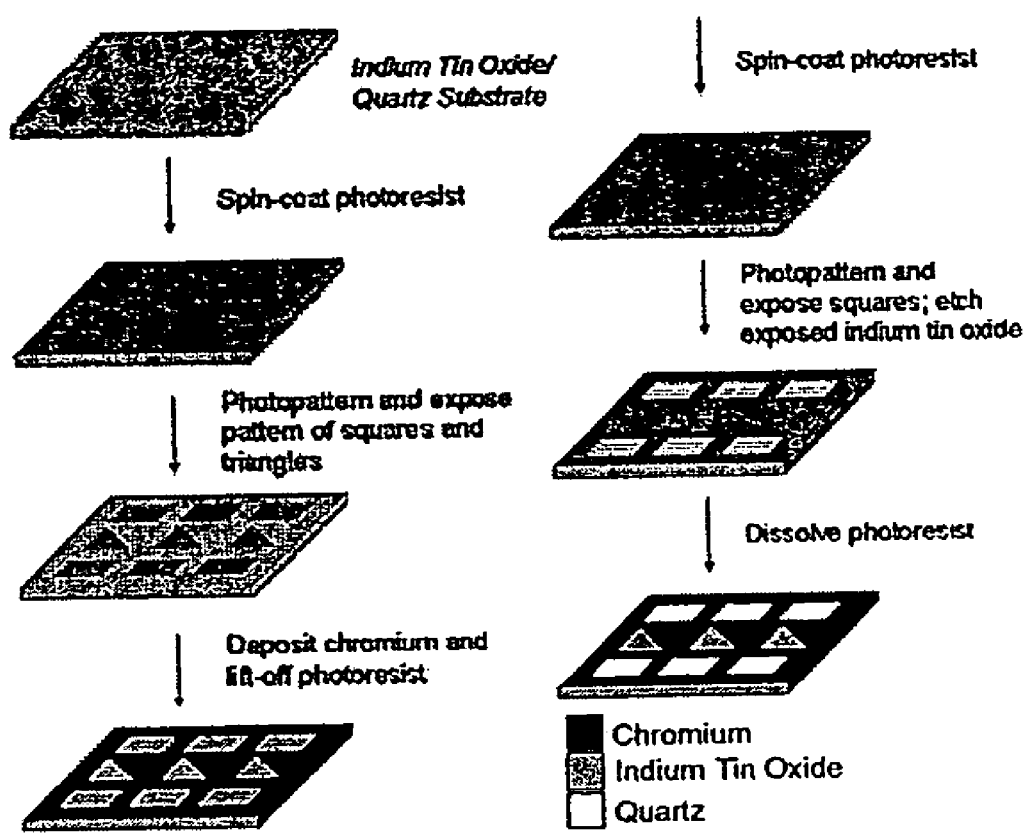
FIG. 3B is a schematic illustration showing the procedure used for fabricating a photomask that allows area-selective transmission of 220 nm light, 365 nm light, and neither of these wavelengths.

To demonstrate photopatterning of SAMs using two different wavelengths of light from a Hg(Xe) arc lamp, a mask was fabricated with an array of squares in quartz and an array of triangles in ITO; the remainder of the mask was rendered opaque using chromium (FIG. 3B). The photomask, once fabricated, could be used repeatedly. The photomask was typically placed 10-50 μm above the gold surface to avoid damaging SAMs on a surface, although only minimal damage (e.g., submicron scratches) was observed in experiments where the mask was placed in contact with the SAM. The photomask was exposed to light at 220 nm (15 mW/cm$^2$, 15 min) and 365 nm (34 mW/cm$^2$, 3 min) in two separate steps because separate mirrors were used to reflect these two wavelengths produced by the Hg(Xe). In other embodiments, a single exposure could be used utilizing a mirror that reflected light at 220 and 365 nm.

The example used a commercially available quartz substrate coated with ITO (supplied by Delta Technologies, 1 mm thick substrate coated with ~200 nm of ITO, 15±5Ω) as the substrate for the photomask. A layer of photoresist (Shipley 1827, 2.7 μm thick) was spun on the substrate. A mask having patterns of squares and triangles was placed on top of the substrate, and this substrate was exposed, forming the pattern of squares and triangles (200 μm or 1 mm sides) in the photoresist. Using electron-beam metal evaporation, a film of chromium (100 nm thick) was deposited on top of the layer of photoresist. The photoresist was dissolved using acetone (3 min) and the substrate was rinsed with isopropyl alcohol, leaving behind indium tin oxide in the square and triangle regions, and chromium in regions that were not covered by the squares and triangles. Using another layer of photoresist (Shipley 1827, 2.7 μm thick) as an etch-mask, ITO was etched selectively in the squares. The etchant solution for ITO consisted of deionized water, HCl, HNO$_3$ (15:4:1, v/v), and a few drops of Triton X-100 (55° C., 10 min). After etching, the substrate was rinsed with deionized water, and the photoresist was removed using acetone (3 min). The substrate was then rinsed with isopropyl alcohol.

A similar fabrication strategy was used for obtaining patterns of multiple, aligned SAMs that resist the adsorption of proteins. The background region (that is not patterned with squares or triangles) comprised ITO, and the triangles comprised a 200 nm thick layer of gold on a 1 nm thick layer of titanium.

Example 3

Patterning Multiple, Aligned SAMs Using Photolithography

This example describes the patterning of a gold substrate with three aligned regions of self-assembled monolayers (SAMs) using one photomask and one set of exposures to light at different wavelengths, but without the need for realignment of photomasks between exposures. This method uses a polyfunctional alkanethiol that forms a SAM on a gold substrate and that presents two types of photocleavable bonds: a photocleavable group that cleaves on exposure to light at 365 nm and a thiolate bond (Au—S) that cleaves on exposure to light at 220 nm.

The multi-wavelength selective photomask was placed 10-50 μm above the gold surface containing the SAM, although the mask could also be placed in direct contact with the SAM. The photomask was exposed to light at 220 nm (15 mW/cm$^2$, 15 min) and 365 nm (34 mW/cm$^2$, 3 min).

Two methods are described: the photopatterning method described by FIG. 1A produced a SAM that terminates in amines after exposure to light at 365 nm, while the method described by FIG. 1B produced a SAM that terminates in primary amides after exposure to light at 365 nm. The method described by FIG. 1B also permits the original SAM to present arbitrary functionality beyond the photocleavable linker. A new SAM can be formed in regions that are exposed to light at 220 nm in both approaches. R in the figure represents any group that can be coupled to a carboxylic acid, e.g., amine, alcohol, etc.; R' in the figure represents any group that contains a carboxylic acid, aldehyde, etc. that can be coupled to an amine; R" in the figure represents an arbitrary functionality that terminates with a thiol group. (Note: alkanethiol SAMs on gold substrates are tilted 30° to the normal and are shown here schematically without any tilt.)

The photopatterning method described by FIG. 1A produced a SAM that terminates in amines after exposure to light at 365 nm. A photocleavable amine-protecting group, 1-(3,4-(methylenedioxy)-6-nitrophenyl)ethylchloroformate (MeNPOC, $(CH_3O)_2C_6H_2NO_2CH(CH_3)OCOCl$), which cleaves quantitatively on photolysis using near-UV light (365 nm) and regenerates the amines, was used (FIG. 1A). MeNPOC does not require the use of solution-phase scavengers. In addition, it is possible to use this surface for further modification: the amines generated by deprotection can be modified using traditional solid-phase synthetic methods.

A second method (FIG. 1B) used a photocleavable linker, 3-[5-(1-amino-ethyl)-2-methoxy-4-nitro-phenoxy]-propionic acid (NPOP, $H_2NCH(CH_3)C_6H_2(OCH_3)O(CH_2)_3CO_2H$), and permitted the alkanethiol to include functional groups beyond the photocleavable group. The o-nitrobenzyl component can be modified to present another chemical functionality, either before or after photopatterning. A SAM that contains NPOP and that is exposed to light at 365 nm is converted to a SAM that terminates in primary amides; these primary amides can, in certain embodiments, be functionalized further (e.g., by reduction to amines with lithium aluminum hydride), if desired.

Example 4

Immunofluorescent Labeling of Photopatterned Mixed SAMs

This example describes the preparation and immunolabeling of a patterned surface comprising multiple, align SAMs using mixed SAM-forming species of $HS(CH_2)_{11}EG_2NPOC$ (5) and $HS(CH_2)_{11}EG_6OH$ on a gold substrate (FIG. 4A).

To form a mixed SAM, gold was first evaporated on a glass slide (Ti, 1 nm; Au, 30 nm). A mask (prepared by a procedure substantially similar to that described in Example 2) was placed on top of a 50-μm Kapton spacer resting on the gold substrate and exposed to light at 365 nm (33.7 mW/cm², 3 min) followed by an exposure to light at 220 nm (15 mW/cm², 15 min). Upon exposure to light at both 220 and 365 nm through the photomask (but without repositioning the mask or substrate between the two exposures), the mixed-SAM substrate was patterned into regions presenting the original SAM, a SAM that terminated in primary amines, and bare gold.

The exposed gold surface was modified with a mixed SAM by incubation with a solution containing $HS(CH_2)_{11}EG_6OH$ (1.9 mM) and $HS(CH_2)_{11}EG_2DNP$ (7) (0.1 mM; DNP, dinitrophenyl); the region that presented a SAM that terminated in amines was modified by reaction with (+)-biotin (as the (+)-biotin N-hydroxysuccinimide ester, Biotin-NHS).

The gold substrate was incubated (60 s) in an ethanolic solution of $HS(CH_2)_{11}(EG)_3DNP$ (0.1 mM) and $HS(CH_2)_{11}(EG)_6OH$ (1.9 mM), resulting in the formation of a mixed SAM in the areas that had been exposed to 220 nm light. The gold substrate was rinsed with ethanol.

Biotin-NHS was coupled to the amines in the region of the SAM that was exposed to light at 365 nm only. To attach Biotin-NHS to the SAM, (+)-Biotin N-hydroxysuccinimide ester (5 mg, 15 μmol) was dissolved in dimethyl sulfoxide (DMSO, 0.5 mL) and sonicated until a clear solution was obtained (60 s). The biotin-NHS solution was diluted immediately before use with 50 mM sodium carbonate buffer (pH 9.55) to obtain a 1.5 mM aqueous solution of biotin-NHS, and the gold substrate was incubated (300 s) in this aqueous solution. The substrate was rinsed with ethanol and dried with compressed nitrogen.

Surface blocking and antibody binding were carried out by successive incubation steps (37° C., 1 h), each followed by rinsing with PBS, as follows. Antibody solutions were diluted to their working concentration using blocking buffer. The substrate was incubated in blocking buffer and then incubated in a mixture of anti-DNP rabbit IgG (1:3.5) and anti-biotin mouse IgG (1:35).

A final incubation step was carried out in a mixture of fluorescently labeled anti-mouse IgG (AF488-anti-mouse IgG (1:10), green in FIG. 4B) and fluorescently labeled anti-rabbit IgG (TR-anti-rabbit IgG (1:10), blue in FIG. 4B). Using these antibodies, a fluorescence signal with an intensity that was indistinguishable from the background was recorded from the original SAM (black in FIG. 4B). (The gold substrate was mounted on a coverslip using H-1000 mounting medium for fluorescence and imaged by fluorescence microscopy.) The resulting immunofluorescence image showed three aligned SAMs in the pattern of the photomask used and, thus, demonstrated the ability to pattern multiple, aligned SAMs using light and a photomask without alignment. A control experiment where anti-DNP rabbit IgG and anti-biotin mouse IgG were replaced by anti-BSA rabbit IgG (1:35) and anti-BSA mouse IgG (1:35) did not show any pattern. Thus, the image shown in FIG. 4B is a result of specific interactions between antigens and antibodies.

Example 5

Patterning and Characterization of Multiple Aligned SAMs That Resist the Adsorption of Proteins This example demonstrates the use of a SAM terminated in a peptide sequence, Gly-Arg-Gly-Asp (GRGD), which is linked to an alkanethiol containing a photocleavable moiety. The photocleavable moiety was used to pattern two aligned SAMs that are resistant to the adsorption of proteins, and a third region that does not resist the adsorption of proteins. The RGD sequence is found within many extracellular matrix (ECM) proteins (fibronectin, laminin, vitronectin, collagens, and proteoglycans), and SAMs that incorporate this peptide sequence are relevant for studies of adhesion of cells to surfaces.

Figure 5:
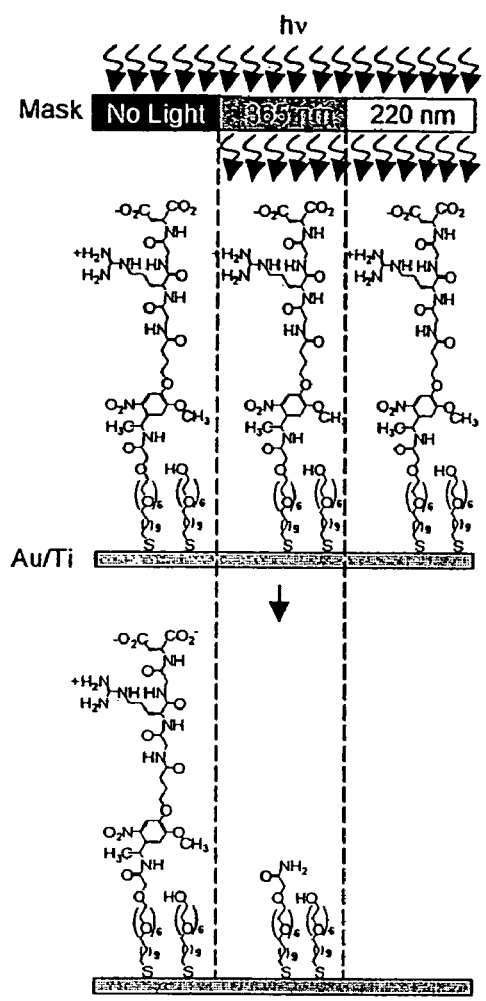
FIG. 5 shows the fabrication and characterization of surfaces containing two SAMs that resist the adsorption of proteins and a surface that does not resist the adsorption of proteins.
Figure 5:
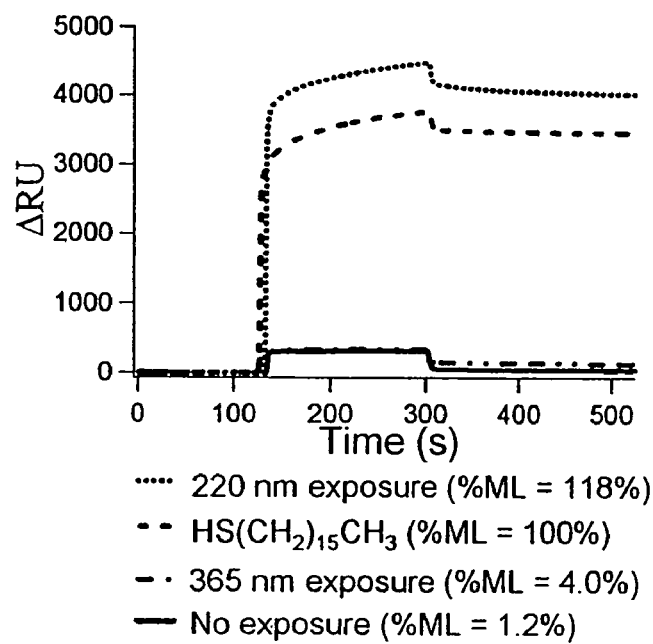

A SAM was formed by incubating an electron-beam-deposited gold surface on a glass slide (Ti, 1 nm; Au, 30 nm) in an ethanolic solution of $HS(CH_2)_{11}EG_6NPOP(GRGD)$, 8 (0.05 mM) and $HS(CH_2)_{11}EG_6OH$ (0.95 mM) over a period of 12 h (FIG. 5). Assuming that the concentration of alkanethiols in solution approximates the concentration of alkanethiols in a SAM, this mixture of alkanethiols produced a SAM containing ~5 mol % $HS(CH_2)_{11}EG_6NPOP(GRGD)$ and ~95 mol % $HS(CH_2)_{11}EG_6OH$ (mol % refers to the ratio of the number of moles of an individual alkanethiol relative to the number of moles of both alkanethiols, expressed as a percentage). In favorable cases, a mixed SAM that comprises at least 50 mol % $HS(CH_2)_{11}EG_6OH$ resists the adsorption of proteins.

Using a procedure similar to that discussed above in Example 3 in the context of FIG. 1B, a mixed SAM of of $HS(CH_2)_{11}EG_6NPOP(GRGD)$ and $HS(CH_2)_{11}EG_6OH$ was illuminated through an area selective mask fabricated in a manner similar to that described in Example 2. Upon exposure to light at 365 nm (33.7 mW/cm², 3 min), the mixed SAM of $HS(CH_2)_{11}EG_6NPOP(GRGD)$ and $HS(CH_2)_{11}EG_6OH$ became $HS(CH_2)_{11}EG_6CONH_2$ and $HS(CH_2)_{11}$ EG$_6$OH, respectively (FIG. 5A), and the surface remained resistant to the adsorption of proteins. After exposure to light at 220 nm (15 mW/cm$^2$, 15 min), the surface no longer resisted the adsorption of proteins. The loss in ability to resist the adsorption of proteins after exposure to light at 220 nm was evidence that the SAM containing HS(CH$_2$)$_{11}$EG$_6$NPOP (GRGD) and HS(CH$_2$)$_{11}$EG$_6$OH was photocleaved.

Using surface plasmon resonance (SPR) spectroscopy, the ability of SAMs exposed to different wavelengths of light to adsorb proteins was characterized. A SAM composed of hexadecanethiol on gold was used as an internal standard; this SAM adsorbs a monolayer of protein, and the change in reflectance due to this monolayer of protein is assigned a value of 100% ML (ML, monolayer; i.e., one monolayer of adsorbed protein). SPR established that a mixed SAM that was assumed to consist of 5 mol % HS(CH$_2$)$_{11}$EG$_6$NPOP (GRGD) and 95 mol % HS(CH$_2$)$_{11}$EG$_6$OH on a gold substrate was resistant to the adsorption of proteins prior to irradiation (FIG. 5B). Referring to FIG. 5B, an SPR sensor gram of the mixed SAMs for substrates that have not been exposed to light, that have been exposed to light at 365 nm, and that have been exposed to light at 220 nm is shown. The original SAM, protected from exposure to light by the opaque, chromium area of the mask, remains resistant to the adsorption of fibrinogen (1 mg/mL, PBS buffer). After exposure to light at 365 nm, the SAM region that terminates in primary amides resists the adsorption of proteins, and after exposure to light at 220 nm, the gold (or oxidized gold) surface (the monolayer is cleaved entirely) is unable to resist the adsorption of proteins.

It is noted that the amount of protein adsorbed on bare gold resulted in an increased % ML value compared with proteins adsorbed on hexadecanethiol SAMs. It is believed that proteins may become denatured to a lesser extent on bare gold surfaces than on hexadecanethiol SAMs; a denatured protein probably presents a larger footprint on the surface and, in turn, limits the amount of protein adsorbed.

Figure 6:
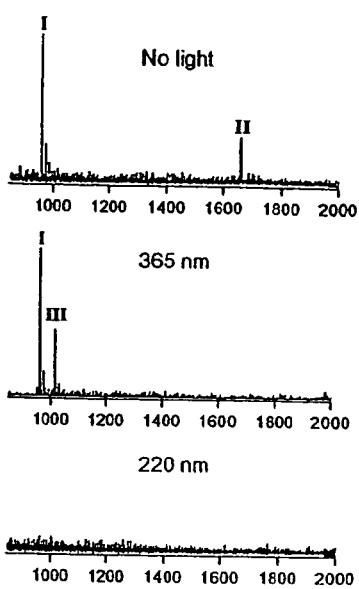
FIG. 6 shows MALDI-TOF mass spectra of samples containing mixed SAMs that have not been exposed to light, that have been exposed to light at 365 nm, and that have been exposed to light at 220 nm. The peak at m/z 958 (1) corresponded to the symmetric disulfide $HOEG_6(CH_2)_{11}SS(CH_2)_{11}EG_6OH$ that is expected to be abundant in the spectra of the mixed SAMs. The initial monolayer displayed a peak at m/z 1659 (II) corresponding to the asymmetric disulfide $HOEG_6(CH_2)_{11}SS(CH_2)_{11}EG_6NPOP(GRGD)$ (expected m/z is 1659). After exposure to light at 365 nm, a peak at m/z 1015 (III) corresponding to the asymmetric disulfide $HOEG_6(CH_2)_{11}SS(CH_2)_{11}EG_6CONH_2$ (expected m/z is 992 plus $Na^+$, m/z 23, gives m/z 1015) was observed. After exposure to light at 220 nm, no peaks were observed, indicating photocleavage of the mixed SAM. No other molecular fragments are expected to be in significant abundance in this region (800<m/<2000) for all three spectra, in agreement with the observed data. The symmetric disulfides (GRGD) $NPOPEG_6(CH_2)_{11}SS(CH_2)_{11}EG_6NPOP(GRGD)$ and $H_2NOCEG_6(CH_2)_{11}SS(CH_2)_{11}EG_6CONH_2$ are unlikely to appear in the mass spectra because of the dilute concentration of the alkanethiol $HS(CH_2)_{11}EG_6NPOP(GRGD)$ present in the original mixed SAM. Although individual alkanethiols corresponding to $HS(CH_2)_{11}EG_6NPOP(GRGD)$ and $HS(CH_2)_{11}EG_6CONH_2$ were observed occasionally, most molecular fragments appeared as disulfides.

Surfaces were also characterized using MALDI-TOF MS (Su, J.; Mrksich, M. *Angew. Chem., Int. Ed.* 2002, 41, 4715-4718.; Su, J.; Mrksich, M. *Langmuir* 2003, 19, 4867-4870). FIG. 6 presents MALDI-TOF mass spectra of samples containing mixed SAMs that have not been exposed to light, that have been exposed to light at 365 nm, and that have been exposed to light at 220 nm. The peak at m/z 958 (I) corresponded to the symmetric disulfide HOEG$_6$(CH$_2$)$_{11}$SS (CH$_2$)$_{11}$EG$_6$OH that is expected to be abundant in the spectra of the mixed SAMs. The initial monolayer displayed a peak at m/z 1659 (II) corresponding to the asymmetric disulfide HOEG$_6$(CH$_2$)$_{11}$SS(CH$_2$)$_{11}$EG$_6$NPOP(GRGD) (expected m/z is 1659). After exposure to light at 365 nm, a peak at m/z 1015(III) corresponding to the asymmetric disulfide HOEG$_6$ (CH$_2$)$_{11}$SS(CH$_2$)$_{11}$EG$_6$CONH$_2$ (expected m/z is 992 plus Na$^+$, m/z 23, gives m/z 1015) was observed. The presence of the peak at m/z 1015 (III) and the absence of a peak at m/z 1659 (II) indicated the photocleavage of the peptide sequence and showed that the remaining SAM terminated in primary amides and hexaethylene glycol groups. After exposure to light at 220 nm, no peaks were observed, indicating photocleavage of the mixed SAM. (No organic species with m/z greater than 350, the lower limit of detection of the mass spectrometer used, was recorded from MS analysis of the SAM after exposure to light at 220 nm.) No other molecular fragments are expected to be in significant abundance in this region (800<m/z<2000) for all three spectra, in agreement with the observed data. The symmetric disulfides (GRGD) NPOPEG$_6$(CH$_2$)$_{11}$SS(CH$_2$)$_{11}$EG$_6$NPOP(GRGD) and H$_2$NOCEG$_6$(CH$_2$)$_{11}$SS(CH$_2$)$_{11}$EG$_6$CONH$_2$ are unlikely to appear in the mass spectra because of the dilute concentration of the alkanethiol HS(CH$_2$)$_{11}$EG$_6$NPOP(GRGD) present in the original mixed SAM. Although individual alkanethiols corresponding to HS(CH$_2$)$_{11}$EG$_6$NPOP(GRGD) and HS(CH$_2$)$_{11}$EG$_6$CONH$_2$ were observed occasionally, most molecular fragments appeared as disulfides.

Spatially resolved MALDI-TOF MS data were obtained by programming a scanner to obtain five mass spectra from 250 µm square regions across the substrate. Each mass spectrum corresponded to either a region containing the original SAM, the SAM after exposure to light at 365 nm, or the bare gold. For the purposes of presentation, an arbitrary color was assigned to each pixel: white for m/z signals representing the original SAM (HOEG$_6$(CH$_2$)$_{11}$SS(CH$_2$)$_{11}$EG$_6$NPOP (GRGD)), gray for m/z signals representing the SAM after exposure to light at 365 nm (HOEG$_6$(CH$_2$)$_{11}$SS (CH$_2$)$_{11}$EG$_6$CONH$_2$), and black for when no m/z signal was detected. A spatial representation of these data using the arbitrary values and their corresponding x-y coordinates was plotted.

Figure 7A:
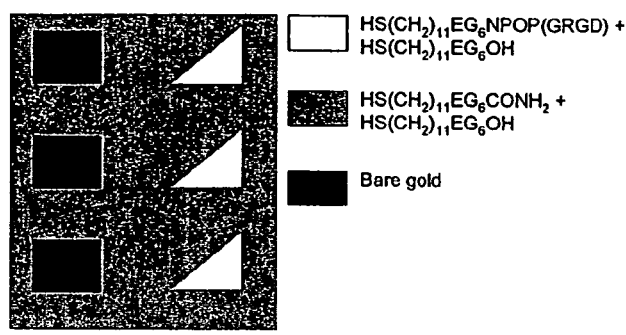
FIG. 7A is a representation of the expected pattern of multiple, aligned SAMs generated from a mixed SAM containing $HS(CH_2)_{11}EG_6NPOP$ (GRGD) and $HS(CH_2)_{11}EG_6OH$.
Figure 7B:
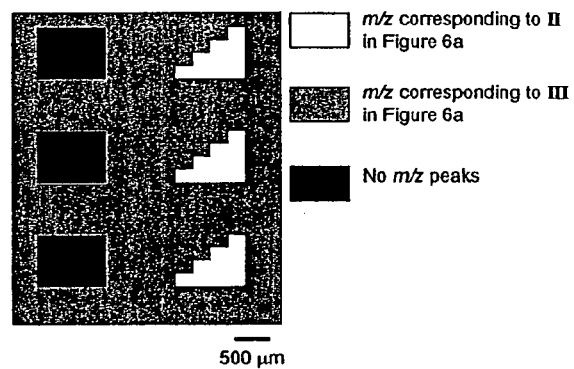
FIG. 7B is a spatially resolved image of multiple, aligned SAMs constructed from the location of m/z peaks obtained using MALDI-TOF and corresponding to $HOEG_6(CH_2)_{11}SS(CH_2)_{11}EG_6NPOP$ (GRGD) (white), $HOEG_6(CH_2)_{11}SS(CH_2)_{11}EG_6CONH_2$ (gray), or no alkanethiol (black). The spatial resolution of our detector is limited to 100 μm.

A substrate was scanned that contained multiple, aligned SAMs (1 cm×1 cm square-region) and the observed m/z peaks were plotted as a function of position on the substrate (FIG. 7). FIG. 7 illustrates that results for the patterning of two regions of aligned SAMs that resist the adsorption of proteins and a third region that does not resist the adsorption of proteins. FIG. 7A illustrates a representation of the expected pattern of multiple, aligned SAMs generated from a mixed SAM containing HS(CH$_2$)$_{11}$EG$_6$NPOP(GRGD) and HS(CH$_2$)$_{11}$EG$_6$OH. FIG. 7B presents a spatially resolved image of multiple, aligned SAMs constructed from the location of m/z peaks obtained using MALDI-TOF and corresponding to HOEG$_6$(CH$_2$)$_{11}$SS(CH$_2$)$_{11}$EG$_6$NPOP(GRGD) (white), HOEG$_6$(CH$_2$)$_{11}$SS(CH$_2$)$_{11}$EG$_6$CONH$_2$ (gray), or no alkanethiol (black). The spatial resolution of the detector used was limited to 100 µm (see below).

The resolution of the resulting plot was limited to about 100 µm, since the spatial resolution of the detector used to acquire individual mass spectra from the patterned substrate was limited to square pixels with a dimension of 100 µm. The spatially resolved plot showed three distinct regions: the original SAM (m/z arising from HOEG$_6$-(CH$_2$)$_{11}$SS (CH$_2$)$_{11}$EG$_6$NPOP(GRGD)), the SAM after exposure to light at 365 nm (m/z arising from HOEG$_6$(CH$_2$)$_{11}$SS(CH$_2$)$_{11}$ EG$_6$CONH$_2$), and the SAM after exposure to light at 220 nm. The expected pattern of multiple, aligned SAMs generated using our photomask is shown in FIG. 7A, and the observed plot of the multiple, aligned SAMs as generated from an analysis of m/z peaks in MS data is shown in FIG. 7B. It may be concluded from both the MS and SPR data that two regions of aligned SAMs were patterned that resist the adsorption of proteins and a third region was also patterned that does not resist the adsorption of proteins. In summary, the patterning of multiple, aligned regions of alkanethiol SAMs that resist the adsorption of proteins has been demonstrated.

Such multiple, aligned patterns of SAMs can be used, as but one of many examples, for patterning multiple cell types and for studying cell-cell signaling (where one cell type is separated from the other on the surface).

Example 6

To demonstrate photopatterning of SAMs using two different wavelengths of light from a lamp, such as an Hg(Xe) arc lamp, a mask was fabricated comprising an array of squares in quartz and an array of triangles in ITO; the remainder of the mask was made opaque using chromium (FIG. 3B).

The photomask, once fabricated, could be used repeatedly. In some cases, the photomask was placed 10-50 µm above the gold surface. In other cases, the photomask was placed in direct contact with the molecules on the surface. In certain embodiments, generation of patterns comprising multiple, aligned molecules requires only a single exposure of light at multiple wavelengths using a photomask having multiple wavelength-selective regions.

The ITO was etched for 10 min, which was found to be the optimal time to expose a uniform quartz region; however, the etchant partially removed metal near the quartz region, and a semitransparent region was produced around metal regions that failed to absorb light at 220 and 365 nm as efficiently as metal that was not etched. These partially exposed regions of ITO are responsible for the blue border around the black pattern in FIG. 4B.

A mixed SAM containing $HS(CH_2)_{11}EG_2NPOC$ and $HS(CH_2)_{11}EG_6OH$ on a gold substrate (FIG. 4A) was used to patterning multiple, aligned SAMs using photolithography. Upon exposure to light at both 220 and 365 nm through the photomask (but without repositioning the mask or substrate between the two exposures), the substrate could be patterned into regions presenting the original SAM, a SAM that terminated in primary amines, and bare gold. The region that presented a SAM that terminated in amines could be modified, for example, by reaction with (+)-biotin (as the (+)-biotin N-hydroxysuccinimide ester), and the exposed gold surface could be modified, for example, with a mixed SAM by incubation with a solution containing $HS(CH_2)_{11}EG_6OH$ (1.9 mM) and $HS(CH_2)_{11}EG_2DNP$ (7) (0.1 mM; DNP, dinitrophenyl). It should be understood that the amine-terminating region can be modified by any appropriate chemical group, using any appropriate technique such as by chemical reaction, protein binding, van der Waals interaction, hydrogen bonding, or physical adsorption. Similarly, the exposed gold surface can be modified by any SAM-forming species, or any technique such as the ones mentioned herein.

Surfaces containing the appropriate attached molecules could be used for specific interactions, for example, for the binding interaction between antigens and antibodies. These surfaces could also be labeled immunofluorescently. For example, the substrate mentioned above could be incubated with anti-biotin mouse IgG and anti-DNP rabbit IgG and then with a mixture of fluorescently labeled anti-mouse IgG (green in FIG. 4B) and fluorescently labeled anti-rabbit IgG (blue in FIG. 4B). Using these antibodies, a fluorescence signal with an intensity that was indistinguishable from the background was recorded from the original SAM (black in FIG. 4B). The resulting immunofluorescence image showed three aligned SAMs in the pattern of the photomask used and, thus, demonstrated the ability to pattern multiple, aligned SAMs using light and a photomask without alignment. A control experiment where anti-DNP rabbit IgG and anti-biotin mouse IgG were replaced by anti-BSA rabbit IgG and anti-BSA mouse IgG did not show any pattern. Thus, it was concluded that the image shown in FIG. 4B is a result of specific interactions between antigens and antibodies.

In certain cases, a photocleavable linker (FIG. 1B) that allowed the alkanethiol to include functional groups beyond the photocleavable linker was used in the formation of multiple, aligned molecules. For example, a peptide sequence, Gly-Arg-Gly-Asp (GRGD), was added to an alkanethiol that comprised a photocleavable linker. The RGD sequence is found within many extracellular matrix (ECM) proteins (fibronectin, laminin, vitronectin, collagens, and proteoglycans), and SAMs that incorporate this peptide sequence are relevant for studies of adhesion of cells to surfaces. A SAM was formed from an ethanolic solution of $HS(CH_2)_{11}EG_6NPOP(GRGD)$, 8 (0.05 mM), and HS $(CH_2)_{11}EG_6OH$ (0.95 mM) on a gold substrate (FIG. 5). Assuming that the concentration of alkanethiols in solution approximates the concentration of alkanethiols in a SAM, this mixture of alkanethiols produced a SAM containing ~5 mol % $HS(CH_2)_{11}EG_6NPOP(GRGD)$ and ~95 mol % $HS(CH_2)_{11}$ $EG_6OH$ (mol % refers to the ratio of the number of moles of an individual alkanethiol relative to the number of moles of both alkanethiols, expressed as a percentage). In some cases, a mixed SAM that comprises at least 50 mol % $HS(CH_2)_{11}EG_6OH$ was found to resist the adsorption of proteins.

In some cases, a photocleavable linker was used to pattern two aligned SAMs that are resistant to the adsorption of proteins and a third region that does not resist the adsorption of proteins. The two aligned SAMs that were resistant to the adsorption of proteins contained, before exposure to light at 365 nm, $HS(CH_2)_{11}EG_6NPOP(GRGD)$ and $HS(CH_2)_{11}$ $EG_6OH$ and, after exposure to light at 365 nm, $HS(CH_2)_{11}EG_6CONH_2$ and $HS(CH_2)_{11}EG_6OH$.

The ability of SAMs exposed to different wavelengths of light to adsorb proteins can be characterized using techniques such as surface plasmon resonance (SPR) spectroscopy. A SAM comprising hexadecanethiol on gold was used as an internal standard; this SAM adsorbs a monolayer of protein, and the change in reflectance due to this monolayer of protein is assigned a value of 100% ML (ML, monolayer; i.e., one monolayer of adsorbed protein). SPR established that a mixed SAM we assumed to comprise 5 mol % $HS(CH_2)_{11}EG_6NPOP(GRGD)$ and 95 mol % $HS(CH_2)_{11}EG_6OH$ on a gold substrate was resistant to the adsorption of proteins prior to irradiation (FIG. 5). This mixed SAM was characterized after exposure to light at 220 and 365 nm. After exposure to light at 365 nm, the surface remained resistant to the adsorption of proteins, and after exposure to light at 220 nm, the surface no longer resisted the adsorption of proteins. The loss in ability to resist the adsorption of proteins after exposure to light at 220 nm was evidence that the SAM containing $HS(CH_2)_{11}EG_6NPOP(GRGD)$ and $HS(CH_2)_{11}EG_6OH$ was photocleaved. It is noted that the amount of protein adsorbed on bare gold results in an increased % ML value compared with proteins adsorbed on hexadecanethiol SAMs. The proteins may be denatured to a lesser extent on bare gold surfaces than on hexadecanethiol SAMs; a denatured protein may present a larger footprint on the surface and, in turn, limits the amount of protein adsorbed. From SPR, it was concluded that a mixed SAM comprising $HS(CH_2)_{11}EG_6NPOP(GRGD)$ and $HS(CH_2)_{11}EG_6OH$ (before exposure to light at 365 nm) as well as a mixed SAM comprising $HS(CH_2)_{11}EG_6CONH_2$ and $HS(CH_2)_{11}EG_6OH$ (after exposure to light at 365 nm) resisted the adsorption of proteins.

The surfaces described herein were also characterized using MALDI-TOF MS. MALDI-TOF MS provided the molecular weights of the components (as the sodium adducts of disulfides, primarily) containing the original SAM (containing $HS(CH_2)_{11}EG_6NPOP(GRGD)$ and $HS(CH_2)_{11}EG_6OH$), the SAM after exposure to light at 365 nm, and the SAM after exposure to light at 220 nm (FIG. 6). In the case of the SAM before exposure to light at 365 and 220 nm (containing $HS(CH_2)_{11}EG_6NPOP(GRGD)$ and $HS(CH_2)_{11}EG_6OH$), a peak at m/z 1659 corresponded to the asymmetric disulfide $HOEG_6(CH_2)_{11}SS(CH_2)_{11}EG_6NPOP$ (GRGD). After exposure to light at 365 nm, a peak appeared at m/z 1015, which corresponded to the asymmetric disulfide $HOEG_6(CH_2)_{11}SS(CH_2)_{11}EG_6CONH_2$. The presence of this peak and the absence of a peak at m/z 1659 indicated the photocleavage of the peptide sequence and showed that the remaining SAM terminated in primary amides and hexaethylene glycol groups. The peak at m/z 958, found in each of the previous spectra, corresponded to the symmetric disulfide $HOEG_6(CH_2)_{11}SS(CH_2)_{11}EG_6OH$ expected to be present in both samples. Since no organic species with m/z greater than 350 (lower limit of detection of our mass spectrometer) was recorded from MS analysis of the SAM after exposure to light at 220 nm, it was concluded that in regions exposed to light at 220 nm, the entire SAM is photocleaved.

A substrate containing multiple, aligned SAMs (1 cm×1 cm square region) was scanned, and the observed m/z peaks as a function of position on the substrate was plotted (FIG. 7). The resolution of the resulting plot was about 100 μm in this example. The spatially resolved plot showed three distinct regions: the original SAM (m/z arising from $HOEG_6$-$(CH_2)_{11}SS(CH_2)_{11}EG_6NPOP(GRGD)$), the SAM after exposure to light at 365 nm (m/z arising from $HOEG_6(CH_2)_{11}SS$ $(CH_2)_{11}EG_6CONH_2$), and the SAM after exposure to light at 220 nm. The expected pattern of multiple, aligned SAMs generated using the photomask is shown in FIG. 7A, and the observed plot of the multiple, aligned SAMs as generated from an analysis of m/z peaks in MS data is shown in FIG. 7B. From both the MS and SPR data, it can be concluded that two aligned SAMs that resist the adsorption of proteins and a third region that does not resist the adsorption of proteins was patterned. In summary, the patterning of multiple, aligned regions of alkanethiol SAMs that resist the adsorption of proteins has been shown.

Example 7

Multiple, Aligned SAMs Used as Etch Resists

This example illustrates that multiple, aligned molecules on surfaces can be used as etch resists. For example, SAMs formed from alkanethiols on gold can resist corrosion by solution-phase chemical etchants. In this example, a chrome adhesion layer was deposited on a silicon substrate, and a layer of gold was deposited on the adhesion layer. This substrate was then incubated in an alkanethiol that included a photocleavable group; exposure of this alkanethiol to 365 nm light cleaved the right-hand portion of the molecule, leaving an amine end-group on the alkanethiol; exposure of the original alkanethiol to 220 nm light cleaved the thiol-gold bond, leaving behind a bare gold region on the substrate. The alkanethiol used in this example was:

and the cleaved portion had a structure:

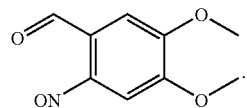

Figure 8:
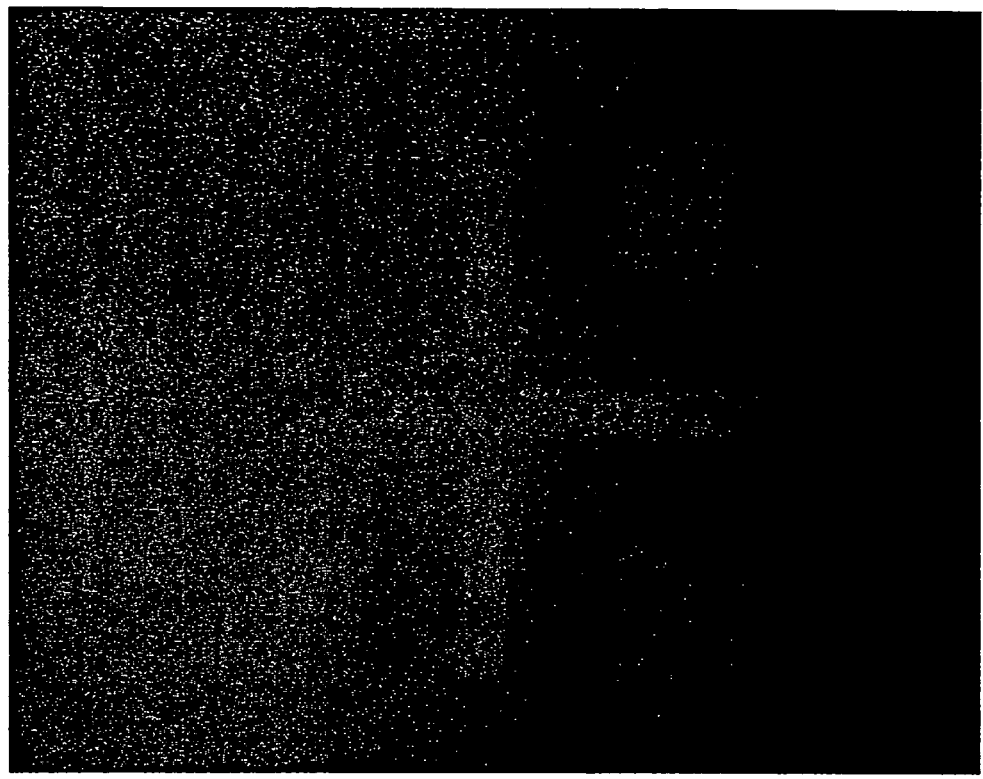
FIG. 8 is a photograph of a surface comprising alkanethiols that was used as an etch resist. The continuous gold film represents a region protected from light at 220 nm and 365 nm. The partial gold film represents a region protected only from 220 nm light, and shows some degree of etching. The chrome/silicon region represents a region exposed to light at 220 nm and 365 nm. Exposure times are as for the published article. Scale bar is 100 microns.
Figure 8:
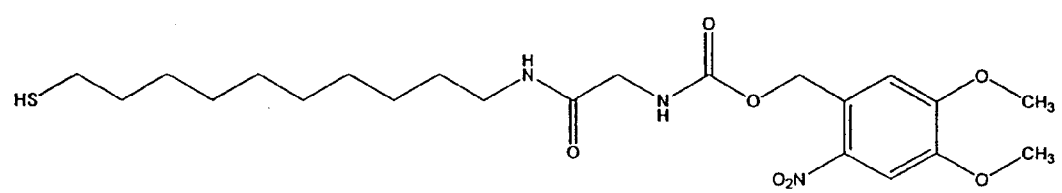

After placing a photomask (that included regions that were transparent at both 220 nm and 365 nm light) on top of the substrate, the substrate was exposed to 220 nm and 365 nm light, and then exposed to an etchant solution. FIG. 8 shows the result of the experiment. The continuous gold film represents a region protected from light at 220 nm and 365 nm. The partial gold film represents a region protected only from 220 nm light, and shows some degree of etching. The chrome/silicon region represents a region exposed to light at 220 nm and 365 nm. Exposure times were similar to those in other experiments requiring exposure. Thus, this example shows that multiple, aligned molecules of discontinuous patterns can be made and used as etch resists on a surface.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

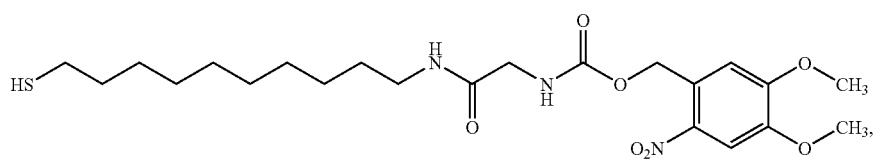

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method comprising acts of:
   providing a surface, at least a portion of which comprises molecules attached thereon;
   exposing the surface to electromagnetic radiation; and
   altering the layer of molecules with the electromagnetic radiation to form a pattern comprising at least a first, second, and third region, wherein
   the first, second, and third regions differ from each other in at least one chemical and/or physical characteristic.

2. A method as in claim 1, wherein the molecules are arranged on the surface in a layer.

3. A method as in claim 2, wherein the layer comprises a monolayer.

4. A method as in claim 3, wherein the monolayer comprises a self-assembled monolayer.

5. A method as in claim 1, wherein the first, second, and third regions differ from each other in their hydrophobicity, ability to resist binding of proteins, ability to bind to cells, and/or ability to be etched by exposure to an etching solution.

6. A method as in claim 1, wherein at least one of the first, second, and third regions of the pattern is non-continuous.

7. A method as in claim 1, wherein each of the first, second, and third regions of the pattern is non-continuous.

8. A method as in claim 1, wherein the exposing act comprises exposing the surface to light of at least a first wavelength and a second wavelength.

9. A method as in claim 1, wherein in the altering act, the pattern is formed by chemically and/or physically altering molecules attached to the surface.

10. A method as in claim 4, wherein the at least a first, second, and third region of the pattern are formed simultaneously.

11. A method as in claim 4, wherein the pattern is formed upon exposing the surface to only a single exposure of the electromagnetic radiation.

12. A method as in claim 8, wherein the exposing act comprises passing light through a photomask having a first region that is substantially transparent to light at the first wavelength but is not substantially transparent to light at the second wavelength.

13. A method as in claim 12, wherein the photomask comprises a second region that is substantially transparent to light at the first wavelength and to light at the second wavelength, and a third region that is not substantially transparent to light at the first or second wavelengths.

14. A method as in claim 9, wherein at least the first region of the pattern is formed via cleavage of at least a portion a molecular species attached on the surface within the first region.

15. A method as in claim 9, further comprising after the altering act:
   exposing at least a portion of the surface with another entity to form a new chemical species attached to the surface.

16. A method as in claim 9, further comprising:
   exposing at least a portion of molecules that have been chemically and/or physically altered in the altering step with another entity to form a new chemical species attached to the surface.

17. A method as in claim 14, wherein at least the second region of the pattern is formed via cleavage of at least a portion a molecular species attached on the surface within the second region.

18. A method as in claim 17, wherein a point of cleavage of the molecular species attached on the surface within the first region is different from a point of cleavage of the molecular species attached on the surface within the second region.

19. A method as in claim 18, wherein the point of cleavage of the molecular species attached on the surface within the second region comprises a bond formed between the surface and the molecular species.

20. A method as in claim 18, wherein the molecules attached to the surface comprise a self-assembled monolayer-forming species that has been bound to the surface, so that the layer of molecules attached to the surface comprises a self-assembled monolayer.

21. A method as recited in claim 18, wherein the molecules attached to the surface comprise a silane moiety containing species that has been bound to the surface.

22. A method as in claim 20, wherein the layer of molecules comprises an alkane thiol that has been bound to the surface.

23. A method as in claim 22, wherein the surface comprises Au, Ag, Pt, Pd, and/or Cu.

24. A method as in claim 20, wherein the self-assembled monolayer-forming species that has been bound to the surface comprises at least a first photoclevable moiety that is able to be cleaved with light having a first wavelength of at least 250 nm.

25. A method as in claim 24, wherein the self-assembled monolayer-forming species that has been bound to the surface further comprises at least one bond connecting at least a portion of a molecule of the species to the surface that is able to be cleaved with light having a wavelength of at least 200 nm but less than the first wavelength.

26. A method as in claim 24, wherein the self-assembled monolayer-forming species that has been bound to the surface does not require presence of scavenger molecules during photocleavage.

27. A method as in claim 21, wherein the surface comprises Si atoms.

28. A method as in claim 27, wherein the surface comprises glass.

29. A method as in claim 1, wherein at least one region of the pattern is characterized by a smallest cross-sectional dimension not exceeding about 10 microns.

30. A method as in claim 1, wherein at least one region of the pattern is characterized by a smallest cross-sectional dimension not exceeding about 1 micron.

* * * * *